US006867177B2

(12) United States Patent
Pinsky

(10) Patent No.: US 6,867,177 B2
(45) Date of Patent: *Mar. 15, 2005

(54) CD39/ECTO-ADPASE AS A TREATMENT FOR THROMBOTIC AND ISCHEMIC DISORDERS

(75) Inventor: David J. Pinsky, Cresskill, NJ (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/374,586

(22) Filed: Aug. 13, 1999

(65) Prior Publication Data

US 2002/0138858 A1 Sep. 26, 2002

(51) Int. Cl.$^7$ ............................. A01N 37/18; C07K 1/00
(52) U.S. Cl. .......................................... 514/2; 530/350
(58) Field of Search ............................ 514/2; 530/350; 435/69.1, 183; 800/8, 9, 13, 18; 424/93.1

(56) References Cited

U.S. PATENT DOCUMENTS 5,798,241 A * 8/1998 Beaudoin et al. ........... 435/188

OTHER PUBLICATIONS

Gura, T., 1997, Science, vol. 278, p. 1041–1042.*
Skolnick et al., 2999, TIBTECH, vol. 18, p. 34–39.*
Rudinger; Characteristics of the amino acids as components of a peptide hormone sequence, 1976, PEPTIDE HORMONES:1–7.*
Kaye et.al.; A single amino acid substitution results in a retinoblastoma protein defective in phosphorylation and oncoprotein binding, 1990, Proc. Natl. Acad. Sci., vol. 87: 6922–6926.*
Fay et al. Arteriosclerosis, Thrombosis, and Vascular Biology. 16(10): 1277–1284, Oct. 1996.*
Gayle et al. Journal of Clinical Investigation. 101(9): 1851–1859, May 1998.*
Guth et al. Journal of Cardiovascualr Pharmacology. 30(2): 261–272, 1997.*
Kaczmarek et al. Journal of Biological Chemistry. 271(51): 33116–33122, Oct. 1996.*
Abstract of McTaggart, et al. (Nov. 2, 1999) Cerebroprotective Role Of CD39 (Endothelial EctoADPase) in Murine Strain, Supplement *Circualtion*, 100(18):Page I–328, 1720 (Exhibit A).
International Search Report for International Application No. PCT/US00/22060, Nov. 14, 2000 (Exhibit C).

GenCore Accession No. WO4334,29 Dec. 1996, Beaudoin et al., WO 96/32471 A2 (UNIV. SHERBROOKE) Oct. 17, 1996 (Exhibit D).
Marcus, et al. (Mar. 1997) The Endothelial Cell Ecto–ADPase Responsible For Inhibition of Platelet Function Is CD39, *The Journal of Clinical Investigation*, 99(6): 1351–1360; (Exhibit E).
Kaczmarek, et al. (Dec. 1996) Identification and Characterization of CD39/Vascular ATP Diphosphohydorlase, *The Journal of Biological Chemistry*. 271(51):33116–33122 (Exhibit F).
Gayle, et al. (May 1998) Inhibition of Platelet Function by Recombinant Soluble Ecto–ADPase/CD39, *The Journal of Clinical Investigation* 101(9): 1851–1859 (Exhibit G); and.
Guth, et al. (1997) Antagonism Of The GPIIb/IIa Receptor With The Nonpeptidic Molecule BIBU52: Inhibition Of Platelet Aggression In Vitro And Antithrombotic Efficacy In Vivo, *Journal of Cardiovascular Pharmacology* 30(2):261–272 (Exhibit H).
Bowie E. J. W., et al., (1974)"The Bleeding Time" Progress in & Hemostasis and Thrombosis, Spaet TH (ed) 2d Ed, New York, Grune Statton, pp. 249–271 (Exhibit 1).
Broekmann, M. J., et al., (1991)"Inhibition of human Platelet Reactivity by Endothelium–Derived Relaxing Factor From Human Umbilical Vein Endothelial Cells in Suspension: Blockade of Aggregation and Secretion by an Aspirin–Insensitive Mechanism", Blood, 78: 1033–1040 (Exhibit 2).
Bronner, L. L., et al., (1995) "Primary prevention of stroke", N. Engl. J. Med. 333(21): 1392–1400 (Exhibit 3).
Buchanan M. R., et al., (1995) "Individual variation in the ASA effects of ASA on platelet function: Implication for the use of clinically", Cardiovasc. Medicine, 11(3):221–227 (Exhibit 4).
Chiu, D., et al.,(1998) "Intravenous tissue plasminogen activator for acute ischemic stroke: feasibility, safety, and efficacy in the first year of clinical practice", Stroke, 29: 18–22 (Exhibit 6).

(List continued on next page.)

*Primary Examiner*—Shin-Lin Chen
(74) *Attorney, Agent, or Firm*—John P. White; Cooper & Dunham LLP

(57) ABSTRACT

The present invention provides a method of treating or preventing thrombotic or ischemic disorders in a subject which comprises administering an agent to the subject, wherein the agent inhibits ADP-mediated platelet aggregation by increasing ADP catabolism, and a method for determining whether a compound inhibits platelet aggregation by increasing ADP catabolism so as to treat or prevent thrombotic or ischemic disorders in a subject, comprising: (a) inducing thrombotic or ischemic disorders in an animal, which animal is an animal model for thrombotic or ischemic disorders; (b) measuring the stroke outcome in the animal, (c) measuring platelet deposition and/or fibrin deposition in ischemic tissue, and (d) comparing the stroke outcome in step (b) and the platelet deposition and/or fibrin deposition with that of the animal model in the absence of the compound so as to identify a compound capable of treating or preventing thrombotic or ischemic disorders in a subject.

6 Claims, 20 Drawing Sheets

OTHER PUBLICATIONS

Choudhri, T. F., et al.,(1997) "Use of a spectrophotometric hemoglobin assay to objectively quantify intracerebral hemorrhage in mice", Stroke, 28: 2296–2302 (Exhibit 7).

Choudhri, T. F., et al.,(1998) "Reduced microvascular thrombosis and improved outcome in acute murine stroke by inhibiting GP IIb/IIIa receptor–mediated platelet aggregation", *J. Clin. Invest.*, 102: 1301–1310 (Exhibit 8).

Connolly, E. S. Jr., et al., (1996) "Cerebral protection in homozygous null ICAM–1 mice after middle cerebral artery occlusion. Role of neutrophil adhesion in the pathogenesis of stroke", J. Clin. Invest., 97: 209–216 (Exhibit 9).

Connolly, E. S. Jr., et al.,(1997) "Exacerbation of cerebral injury in mice which express the P–selectin gene: identification of P–selectin blockade as a new target for the treatment of stroke",Circ. Res., 81: 304–310 (Exhibit 10).

Connolly, E. S. Jr., et al., (1996) "Procedural and strain–related variables significantly affect outcome in a murine model of focal cerebral ischemia", Neurosurg., 38(3): 523–532 (Exhibit 11).

Eippel, D., (1998) "The results of CAPRIE, IST, and CAST", Thrombosis Res., 92: S13–S16 (Exhibit 12).

Eitzman D. T., (1996) "Bleomycin–induced pulmonary fibrosis in transgenic mice that either lack or overexpress the murine plasminogen activator inhibitor–I gene", J. Clin. Invest., 97:232–237 (Exhibit 13).

Erickson, L. A., et al., (1990)" Development of venous occlusions in mice transgenic for the plasminogen activator inhibitor–I gene", Nature, 346: 74–76 (Exhibit 14).

Gayle, R. B., et al., (1998) "Inhibition of platelet function by recombinant soluble ecto–ADPase/CD39",J. Clin. Invest, 101: 1851–1859 (Exhibit 15).

Grotenmeyer, K. H., (1991)"Effects of acetylsalicylic acid in stoke patients; evidence of nonresponders in a subpopulation of treated patients", Thrombosis Res., 63: 587–593 (Exhibit 16).

Handa, M., & Guidotti, G., (1996)"Purification and Cloning of a Soluble ATP–Diphosphohydrolase (Apyrase) from Potato Tubers (*Solanum tubersum*)", Biochem. Biophys. Res. Commun., 218, 916–923 (Exhibit 17).

Harbison, J. W., (1998)" Clinical considerations in selecting Pharm antiplatelet therapy in cerebrovascular disease", Am. J. Health Syst. 55, S17–S20 (Exhibit 18).

Hechler, B., et al., (1998) "The $P2Y_1$ receptor, necessary but not the sufficient to support full ADP–induced platelet aggregation, is not target of the drug clopidogrel", Br. J. Haematol., 103: 858–866 (Exhibit 19).

Huang, Z., et al., (1994)"Effects of Cerebral Ischemia in Mice Deficient Neuronal Nitric Oxide Synthase", Science, 265:1883–1885 (Exhibit 20).

Koch, R., Verhandlungen des X. Internationalem Medizinischen Congresses Berlin 1: 35–47 (1891).(Abstract) (Exhibit 21).

Lawson C. A., et al.,(1997) "Monocytes and tissue factor promote 99: thrombosis in a murine model of oxygen deprivation", J. Clin. Invest., 1729–1738 (Exhibit 22).

Maeda K, et al.,(1998) "Differences in the cerebrovascular anatomy of C57black/6 and SV129 mice", Neuroreport, 9(7):1317–1319 (Exhibit 23).

Majid A., et al., (1999) "Intrinsic, hemodynamic–independent differences in vulnerability to permanent focal cerebral ischemia in common mutant mouse strains", 24th American Heart Association International Conference on Stoke and Cerebral CXJO–XXPY (Exhibit 24).

Maliszewski, C. R., et al., (1994)"The CD39 lymphoid cell activation antigen: Molecular cloning and structural characterization", J. Immunol., 153: 3574–3583 (Exhibit 25).

Marcus, A. J.,& Safeir, L. B.,(1993) "Thromboregulation: multicellular modulation of platelet reactivity in hemostasis and thrombosis", FASEB J., 7: 516–522 (Exhibit 26).

Marcus, A. J., (1999)"Platelets: Their role in hemostasis, thrombosis, and inflammation", In Inflammation: Basic Principles and Clinical Correlates (EDS Gallin, J.I. & Snyderman, R.: 77–95 (Lippincott, Williams & Wilkins, Philadelphia (Exhibit 27).

Marcus, A. J., et al., (1997) "The endothelial cell ecto–ADPase responsible for inhibition of platelet function is CD39", J. Clin. Invest., 99: 1351–1360 (Exhibit 28).

Marcus, A. J., et al., (1991)"Inhibition of platelet function by an aspirin–insensitive endothelial cell ADPase", J. Clin. Invest., 88: 1690–1696 (Exhibit 29).

Mayadas, T. N., et al., (1993) "Leukocyte rolling and extravasation are severely compromised in P–selection deficient mice", Cell, 74(3): 541–554 (Exhibit 30).

Mizutani H, et al.,(1990) "Analyses of thrombocytopenia in idiopathic thrombocytopenic purpura–prone mice by platelet experiments between (NZW X $BXSB)F_1$ and normal mice", Blood, 75:1809–1912 (Exhibit 31).

Naka, Y., et al., (1995) "Enhanced preservation of orthotopically transplanted rat lungs by nitroglycerin but not hydralazine: Requirement for graft vascular homeostasis beyond harvest vasodilation", Circ. Res., 76: 900–906 (Exhibit 32).

Schoenborn, M. A., et al., (1998) "Gene structure and chromosome location of mouse Cd39 coding for an ecto–apyrase", Cytogen Cell Gen., 81(3–4): 287–280 (Exhibit 33).

Wardlaw, J. M., et al., (1997) "Systematic review of evidence on thrombolytic therapy for acute ischemic stroke [see comments]", Lancet., 350: 607–614 (Exhibit 34); and.

Wang, T. F., & Guidotti, G., (1996)"CD39 is an Ecto–($Ca^{2+}$, $Mg^{2+}$)—apyrase", J. Biol. Chem. 271: 9898–9901 (Exhibit 35).

Steering Committee, Lancet, (1986) "A Randomised, Blinded Trial of Clopidogrol versus Aspirin in Patients at Risk of Ischaemic Events" CAPRIE 348:1329–1339.

Wang, T.F., and Guidotti, G., (1996) "CD39 is an Ecto–($Ca^{2+}$, $Mg^{2+}$) –Apyrase", J. Biol. Chem. 271:9898–9901.

\* cited by examiner

SEQUENCE LISTING

```
<160> NUMBER OF SEQ ID NOS: 2

<210> SEQ ID NO 1
<211> LENGTH: 510
<212> TYPE: PRT
<213> ORGANISM: HOMO-SAPIEN

<400> SEQUENCE: 1

Met Glu Asp Thr Lys Glu Ser Asn Val Lys Thr Phe Cys Ser Lys Asn
 1               5                  10                  15

Ile Leu Ala Ile Leu Gly Phe Ser Ser Ile Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255
```

-continued

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
            275                 280                 285

Lys Val Val Asn Val Ser Asp Leu Tyr Lys Thr Pro Cys Thr Lys Arg
            290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
            355                 360                 365

Phe Leu Asn Leu Thr Ser Glu Lys Val Ser Gln Glu Lys Val Thr Glu
            370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Gln Gly Tyr His Phe Thr Ala Asp
            420                 425                 430

Ser Trp Glu His Ile His Phe Ile Gly Lys Ile Gln Gly Ser Asp Ala
            435                 440                 445

Gly Trp Thr Leu Gly Tyr Met Leu Asn Leu Thr Asn Met Ile Pro Ala
450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
            500                 505                 510

<210> SEQ ID NO 2
<211> LENGTH: 439
<212> TYPE: PRT
<213> ORGANISM: Homo sapiens

<400> SEQUENCE: 2

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly

-continued

```
            115                 120                 125
Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Gln Asn Gln Thr
            180                 185                 190

Ile Glu Ser Pro Asp Asn Ala Leu Gln Phe Arg Leu Tyr Gly Lys Asp
        195                 200                 205

Tyr Asn Val Tyr Thr His Ser Phe Leu Cys Tyr Gly Lys Asp Gln Ala
    210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255

Ser Asp Leu Tyr Lys Thr Pro Cys Thr Lys Arg Phe Glu Met Thr Leu
            260                 265                 270

Pro Phe Gln Gln Phe Glu Ile Gln Gly Ile Gly Asn Tyr Gln Gln Cys
        275                 280                 285

His Gln Ser Ile Leu Glu Leu Phe Asn Thr Ser Tyr Cys Pro Tyr Ser
    290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Phe Val Met Lys Phe Leu Asn Leu Thr
                325                 330                 335

Ser Glu Lys Val Ser Gln Glu Lys Val Thr Glu Met Met Lys Lys Phe
            340                 345                 350

Cys Ala Gln Pro Trp Glu Glu Ile Lys Thr Ser Tyr Ala Gly Val Lys
        355                 360                 365

Glu Lys Tyr Leu Ser Glu Tyr Cys Phe Ser Gly Thr Tyr Ile Leu Ser
    370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
                405                 410                 415

Tyr Met Leu Asn Leu Thr Asn Met Ile Pro Ala Glu Gln Pro Leu Ser
            420                 425                 430

Thr Pro Leu Ser His Ser Thr
            435
```

CD39/ECTO-ADPASE AS A TREATMENT FOR THROMBOTIC AND ISCHEMIC DISORDERS

The invention described herein was made in the course of work done under Grant Nos. HL-47073, HL-46403, HL-07423 (AJM, MJB, JHFD), HL-59488 and HL-55397 (DJP) and NS 02038 (ESC) Department of Veterans Affairs and from National Institutes of Health. Therefore, the United States Government has certain rights in this invention.

Throughout this application, various publications are referenced by numbers. Full citations for these publications may be found listed numerically at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Stroke is the third leading cause of death and the main cause of permanent morbidity in the United States, affecting over 450,000 patients annually[1]. Recent studies in a murine model of ischemic stroke demonstrated a pivotal role for platelets in progressive microvascular thrombosis distal to the primary obstruction of a major cerebrovascular tributary[2]. This progressive microvascular thrombosis is characterized by distal platelet and fibrin accumulation, resulting in postischemic hypoperfusion ("no re-flow") and neuronal injury[2]. While leukocyte adhesion receptors and recruited neutrophils contribute to postischemic hypoperfusion, postischemic hypoperfusion cannot be completely abrogated because even in the absence of neutrophils, progressive microvascular thrombosis persists[3,4]. Two thrombolytic agents, recombinant tissue-type plasminogen activator (rtPA) and pro-urokinase, have been used for treatment of stroke. However, their therapeutic utility is limited due to risk of symptomatic and fatal intracranial hemorrhage[5]. In the United States, less than 1% of patients presenting to community hospitals with acute ischemic stroke receive rtPA[6]. Inhibition of the final common pathway of platelet accumulation, via blockade of glycoprotein IIb/IIIa receptor-mediated platelet-platelet interactions, does reduce microvascular thrombosis in experimental stroke[2]. However, as with thrombolytic agents, small excesses of a GPIIb/IIIa receptor blocker culminated in serious intracerebral hemorrhage. It is therefore important to identify novel strategies for inhibition of platelet function in acute stroke that will reduce intravascular thrombosis without increasing risk of intracerebral hemorrhage.

SUMMARY OF THE INVENTION

The present invention provides a method of treating or preventing thrombotic or ischemic disorders in a subject which comprises administering an agent to the subject, wherein the agent inhibits platelet aggregation by increasing ADP catabolism. The present invention also provides a method for determining whether a compound inhibits platelet aggregation by increasing ADP catabolism so as to treat or prevent thrombotic or ischemic disorders in a subject, comprising: (a) inducing thrombotic or ischemic disorders in an animal, which animal is an animal model for thrombotic or ischemic disorders; (b) measuring the stroke outcome in said animal, (c) measuring platelet deposition and/or fibrin deposition in ischemic tissue, and (d) comparing the stroke outcome in step (b) and the platelet deposition and/or fibrin deposition with that of the animal model in the absence of the compound so as to identify a compound capable of treating or preventing thrombotic or ischemic disorders in a subject.

DETAILED DESCRIPTION OF THE INVENTION

Figure 1A:
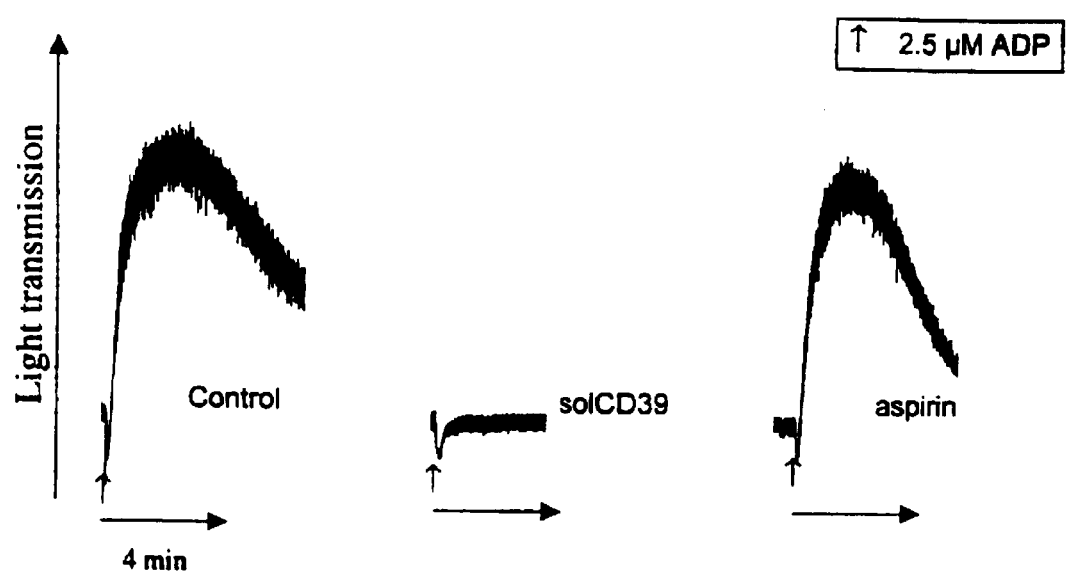
FIGS. 1A–1F: Effects of saline (control), aspirin or CD39 on the aggregation of murine platelets ion response to: (A) ADP 2.5 μM; (B) collagen 2.5 μg/mL; (C) ADP 10 μM; (D) collagen 10 μg/mL; or (E) sodium arachidonate (0.1 mM). The % inhibition of platelet aggregation is shown in (F) Agents were administered to mice 45 minutes prior to harvest of blood, and preparation of platelet-rich plasma for the indicated studies.

The present invention provides a method for treating or preventing stroke in a subject wherein the subject is susceptible to intracranial hemorrhaging, comprising administering a CD39 polypeptide (SEQ ID NO:1) or an active fragment thereof which inhibits adenosine diphosphate-mediated platelet aggregation by increasing adenosine diphosphate catabolism to the subject.

In one embodiment of the method, the active fragment is CD39 polypeptide is a mutated or a truncated form of CD39 polypeptide.

In another embodiment of the method, the active fragment is soluble CD39 (SEQ ID NO:2).

In another embodiment of the method, the CD39 polypeptide is a recombinant CD39 polypeptide having IL-2 as its leader sequence.

In another embodiment of the method, the recombinant CD39 polypeptide lacks a transmembrane domain.

In another embodiment of the method, the active fragment comprises from amino acid number 1 to amino acid number 50 of SEQ ID NO.:2.

In another embodiment of the method, the active fragment of the CD39 polypeptide comprises about 20–80 amino acid residues of SEQ ID NO:1 which mimics the active site of CD39.

In one embodiment of the method, the CD39 polypeptide or its active fragment treats or prevents thrombotic or ischemic disorders in a subject without increasing bleeding or intracerebral hemorrhage.

As used herein, the term "ADP" means adenosine diphosphate.

As used herein, "ischemic and thrombotic disorders" encompass pulmonary embolism, lung ischemia, limb or gut ischemia, myocardial ischemia, post surgical vasculopathy, postangioplasty stenosis, shunt/fistula remodeling or thrombosis, cerebral ischemia, or ischemia of other organs or tissues.

As used herein, the term "ischemic disorder" encompasses and is not limited to a peripherial vascular disorder, a venous thrombosis, a pulmonary embolus, a myocardial infarction, a transient ischemic attack, lung ischemia, unstable angina, a reversible ischemic neurological deficit, adjunct thromolytic activity, excessive clotting conditions, reperfusion injury, sickle cell anemia, a stroke disorder or an iatrogenically induced ischemic period such as angioplasty.

As used herein, the term "thrombotic disorder" encompasses disorders caused by the formation, development or presence of a blood clot or a blood coagulation which is located inside of a patient or inside of an extracorporeal circuit or system which circulates blood of the patient. Thrombotic disorder also encompasses disorders caused by the presence of a thrombus which includes a blood clot partially or fully occluding a blood vessel or formed in a heart cavity or by the activation of a plasmatic coagulation system in a patient which includes the production of fibrin, emeshed platelets, fibrin degradation product, protein C, free protein S, coagulation factor II, immunoglobulin G or albumin in the patient. Thrombotic disorder also encompasses disorders cause by the formation of white thrombus which may be composed of platelets and fibrin and is relatively poor in erythrocytes, a disseminated fibrin deposit thrombus or a red thrombus which may be composed of red cells and fibrin.

In another embodiment of the method, the CD39 polypeptide or its active fragment can be replace by a peptide, an enzyme, a pseudo enzyme, a catalyst, a peptidomimetic compound, a glycosylated peptide, a small molecule, a mutated peptide or an antibody.

As used herein, a polypeptide is an amino acid polymer of amino acids linked together by peptide bonds; a nucleic acid is a deoxyribonucleotide or ribonucleotide polymer of nucleotides linked together by phosphodiester bonds; an antisense nucleic acid is a nucleic acid that is the reverse complement of another nucleic acid which may be capable of inhibiting transcription or translation of the other nucleic acid.

In another embodiment of the method, the the CD39 polypeptide or its active fragment agent comprises a CD39 polypeptide (abbreviated as CD39) or a variant thereof.

Variants in amino acid sequence of CD39 are produced when one or more amino acids in naturally occurring CD39 is substituted with a different natural amino acid, an amino acid derivative, a synthetic amino acid, an amino acid analog or a non-native amino acid. Particularly preferred variants include homologous CD39 of humans or of different species of animals. Variants of a CD39 may include biologically active fragments of naturally occurring CD39, wherein sequences of the variant differ from the wild type CD39 sequence by one or more conservative amino acid substitutions. Such substitutions typically would have minimal influence on the secondary structure and hydrophobic nature of the CD39. The amino acid sequences of CD39 and one variant of CD39 have been previously determined and are the following:

```
MEDTKESNVKTFCSKNILAILGFSSIIAVIALLAVGLTQNKALPENVKYGIVLDAGS    (SEQ ID NO:1)

SHTSLYIYKWPAEKENDTGVVHQVEECRVKGPGISKFVQKVNEIGIYLTDCMERARE

VIPRSQHQETPVYLGATAGMRLLRMESEELADRVLDVVERSLSNYPFDFQGARIITG

QEEGAYGWITINYLLGKFSQKTRWFSIVPYETNNQETFGALDLGGASTQVTFVPQNQ

TIESPDNALQFRLYGKDYNVYTHSFLCYGKDQALWQKLAKDIQVASNEILRDPCFHP

GYKKVVNVSDLYKTPCTKRFEMTLPFQQFEIQGIGNYQQCHQSILELFNTSYCPYSQ

CAFNGIFLPPLQGDFGAFSAFYFVMKFLNLTSEKVSQEKVTEMMKKFCAQPWEEIKT

SYAGVKEKYLSEYCFSGTYILSLLLQGYHFTADSWEHIHFIGKIQGSDAGWTLGYML

NLTNMIPAEQPLSTPLSHSTYVFLMVLFSLVLFTVAIIGLLIFHKPSYFWKDMV

TQNKALPENVKYGIVLDAGSSHTSLYIYKWPAEKENDTGVVHQVEECRVKGPGISKF    (SEQ ID NO:2)

VQKVNEIGIYLTDCMERAREVIPRSQHQETPVYLGATAGMRLLRMESEELADRVLDV

VERSLSNYPFDFQGARIITGQEEGAYGWITINYLLGKFSQKTRWFSIVPYETNNQET

FGALDLGGASTQVTFVPQNQTIESPDNALQFRLYGKDYNVYTHSFLCYGKDQALWQK

LAKDIQVASNEILRDPCFHPGYKKVVNVSDLYKTPCTKRFEMTLPFQQFEIQGIGNY

QQCHQSILELFNTSYCPYSQCAFNGIFLPPLQGDFGAFSAFYFVMKFLNLTSEKVSQ

EKVTEMMKKFCAQPWEEIKTSYAGVKEKYLSEYCFSGTYILSLLLQGYHFTADSWEH

IHFIGKIQGSDAGWTLGYMLNLTNMIPAEQPLSTPLSHST
```

Variants may also have sequences which differ by one or more non-conservative amino acid substitutions, deletions or insertions which do not abolish the biological activity associated with CD39. Conservative substitutions (substituents) typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

A CD39 variant of this invention includes a CD39 varied by changes such as insertions, deletions and substitutions, either conservative or nonconservative where such changes might provide for certain advantages in their use such as increased potency, bioavailability, stability or decreased toxicity or degradation under physiological conditions.

One embodiment of the present invention is a truncated variant of the CD39 which variant is capable of increasing adenosine diphosphate catabolism or having improved availability or decreased immunogenicity or increased activity.

In other embodiments, variants with amino acid substitutions which are less conservative may also result in desired derivatives of CD39, e.g., by causing desirable changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Just as it is possible to replace substituents of the scaffold (i.e., amino acids which make up the CD39), it is also possible to substitute functional groups which decorate the scaffold with groups characterized by similar features (i.e., R-groups which are part of each amino acid). These substitutions will initially be conservative, i.e., the replacement group will have approximately the same size, shape, hydrophobicity and charge as the original group. Non-sequence modifications may include, for example, in vivo or in vitro chemical derivatization of portions of naturally occurring CD39, as well as changes in acetylation, methylation, phosphorylation, carboxylation or glycosylation.

In a further embodiment the CD39 is modified by chemical modifications in which activity is preserved. For example, the CD39 may be aminated, sulfated, singly or multiply halogenated, alkylated, carboxylated, or phosphorylated. The CD39 may also be singly or multiply acylated, such as with an acetyl group, with a farnesyl moiety, or with a fatty acid, which may be saturated, monounsaturated or polyunsaturated. The fatty acid may also be singly or multiply fluorinated. The invention also includes methionine analogs of CD39, for example the methionine sulfone and methionine sulfoxide analogs. The invention also includes salts of CD39, such as ammonium salts, including alkyl or aryl ammonium salts, sulfate, hydrogen sulfate, phosphate, hydrogen phosphate, dihydrogen phosphate, thiosulfate, carbonate, bicarbonate, benzoate, sulfonate, thiosulfonate, mesylate, ethyl sulfonate and benzensulfonate salts.

Variants of CD39 may also include peptidomimetic compounds of CD39. Such compounds are well known to those of skill in the art and are produced through the substitution of certain R groups or amino acids in the protein with non-natural replacements. Such substitutions may increase the stability, bioavailability, or activity of such CD39 compound.

In another embodiment of the method, the CD39 polypeptide is a recombinant CD39 polypeptide having IL-2 as its leader sequence. A different leader sequence may be used to drive the secretion of the protein.

In another embodiment of the method, the recombinant CD39 polypeptide lacks a transmembrane domain.

In another embodiment of the method, the agent comprises a biologically active fragment of the CD39 polypeptide or its variants thereof or a non-protein compound that augments ADP catabolism.

In another embodiment of the method, the active fragment of the CD39 polypeptide has 20–80 amino acid residues which mimics the active site of CD39 or its variants thereof.

In another embodiment of the method, the CD39 polypeptide or its active fragment can be replaced by a nucleic acid encoding CD39 or its variants or a biologically active fragment thereof.

In another embodiment of the method, the stroke is associated with pulmonary embolism, post surgical vasculopathy, postangioplasty stenosis, and shunt/fistula remodeling or thrombosis.

In another embodiment of the method, the stroke is associated with lung ischemia, limb ischemia, gut ischemia, myocardial ischemia.

In another embodiment, the time of administration comprises from about 5 days before surgery or onset of the disorder to about 5 days after surgery or the onset of the disorder. In another embodiment, the period of time comprises from about 1 hour before surgery or the onset of the disorder to about 12 hours after surgery or the onset of the disorder. In another embodiment, the period of time comprises from about 12 hours before surgery or the onset of the disorder to about 1 hour after surgery or the onset of the disorder. In another embodiment, the period of time comprises from about 1 hour before surgery or the onset of the disorder to about 1 hour after surgery or the onset of the disorder.

In one embodiment, the subject is a mammal. In another embodiment, the mammal is a human. In another embodiment, the amount of CD39 polypeptide or its active fragment administered comprises from about 75 $\mu$g/kg to about 550 $\mu$g/kg. In another embodiment, the amount comprises 300 $\mu$g/kg.

In another embodiment of the method, the administration of the CD39 polypeptide or its active fragment occurs at the onset of stroke in a subject.

In another embodiment of the method, the administration of the CD39 polypeptide or its active fragment is prior to stroke onset in a subject.

In another embodiment of the method, the administration of the CD39 polypeptide or its active fragment occurs after the stroke onset in a subject.

In another embodiment of the method, the CD39 polypeptide or its active fragment is administered in a dosage of 1–20 mg/kg of the subject's body weight.

In another embodiment of the method, the CD39 polypeptide or its active fragment is administered in a dosage of 4–8 mg/kg of the subject's body weight.

In another embodiment of the method, the subject is a mouse, a rat, a dog, a primate or a human.

In a further embodiment of the method, the CD39 polypeptide or its active fragment is administered with a pharmaceutically acceptable carrier.

The present invention also provides a method for determining whether a compound inhibits platelet aggregation by increasing ADP catabolism so as to treat or prevent thrombotic or ischemic disorders in a subject, comprising: (a) inducing thrombotic or ischemic disorders in an animal, which animal is an animal model for thrombotic or ischemic disorders; (b) measuring the stroke outcome in said animal, (c) measuring platelet deposition and/or fibrin deposition in ischemic tissue, and (d) comparing the stroke outcome in step (b) and the platelet deposition and/or fibrin deposition with that of the animal model in the absence of the compound so as to identify a compound capable of treating or preventing thrombotic or ischemic disorders in a subject.

In one embodiment of the method, the animal model comprises CD39-deficient mice; wherein the thrombotic or ischemic disorders are induced by administering an agonist to said mice.

In another embodiment of the method, the compound treat or prevent thrombotic or ischemic disorders in a subject without increasing intracerebral hemorrhage or bleeding.

In another embodiment of the method, the stroke outcome is determined from the measurements of platelet deposition, bleeding time and infarction volume.

In another embodiment of the method, the compound can be administered orally or by injection.

In another embodiment of the method, the compound is identified by the method.

In another embodiment of the method, the administration of the compound is prior to stroke onset in the animal.

In yet another embodiment of the method, the administration of the compound occurs at the onset of stroke in the animal.

In a further embodiment of the method, the administration of the compound occurs after the stroke onset in the animal.

The present invention further provides a pharmaceutical composition comprising the compound of identified by the methods and a pharmaceutically acceptable carrier as an agent to treat thrombotic or ischemic disorders in a subject.

In one embodiment of the pharmaceutical composition, the composition comprises CD39 and a pharmaceutically acceptable carrier As used herein, the term "pharmaceutically acceptable carrier" encompasses any of the standard pharmaceutically acceptable carriers, such as phosphate buffered saline solution, water, emulsions such as oil/water emulsion or a triglyceride emulsion, various types of wetting agents, tablets, coated tablets and capsules. Typically, such carriers contain excipients such as starch, milk, sugar, certain types of clay, gelatin, stearic acid, talc, vegetable fats or oils, gums, glycols, or other known excipients. Such carriers may also include flavor and color additives or other ingredients.

By means of well-known techniques such as titration and by taking into account the observed pharmacokinetic characteristics of the agent in the individual subject, a skilled artisan can determine the appropriate dosages for treatment methods of the present invention.

Mutants or fragments of CD39 can be produced by known genetic engineering techniques, using as the starting material recombinant cDNA encoding CD39 in an appropriate cloning vector or using direct chemical synthesis.

This invention will be better understood from the Experimental Details which follow. These sections are set forth to aid in an understanding of the invention but are not intended to, and should not be construed to, limit in any way the invention as set forth in the claims which follow thereafter.

Experimental Details

EXAMPLE 1

CD39/Ecto-ADPase Inhibits Thrombosis and Limits Ischemic Cerebral Injury in Wild Type and Reconstituted CD39 Null Mice Initial studies demonstrated a significant contribution of leukocyte adhesion receptors and recruited neutrophils to postischemic no-reflow, but even in the absence of neutrophils, postischemic no-reflow was not completely abrogated as progressive microvascular thrombosis ensued[3, 4]. More recent studies in a murine model of ischemic stroke demonstrated the cardinal role of platelets in progressive microvascular thrombosis distal to the site of primary obstruction of a major cerebrovascular tributary.[2] Progressive microvascular thrombosis, characterized by accumulation of platelets and fibrin at downstream sites, contributes to post-ischemic hypoperfusion (no reflow) and cerebral tissue damage[2]. Recent research has indicated that inhibition of the final common pathway of platelet accumulation, via blockage of glycoprotein IIb/IIIa receptor-mediated platelet-platelet interactions, could reduce microvascular thrombosis in stroke[2]. However, the therapeutic window for GP IIb/IIIa receptor blockade, similar to thrombolytic agents is narrow, with even small excesses dosing culminating devastating intracerebral hemorrhage.

When the integrity of the blood vessel wall is compromised, platelets adhere to collagen in the subendothelium, leading to platelet activation and the release of additional agonist: adenosine diphosphate (ADP), thromboxane ($TXA_2$), and serotonin. Of these, ADP is the most important platelet agonist and recruiting agent present in the microenvironment of the thrombus[7]. There are three primary mechanisms by which endothelial cells, under homeostatic conditions, maintain blood fluidity at the blood/vessel wall interface. These include the local generation of nitric oxide, release of eicosanoids, and expression of ectoADPase (CD39), a highly conserved enzyme which promotes ADP catabolism, thus potently inhibiting platelet aggregation[8]. Endothelial cells express CD39 constitutively. When recombinant CD39 was transfected into COS cells, they acquired the ability to inhibit ADP-induced platelet aggregation, establishing CD39 as a prime thromboregulatory enzyme[9]. Recently, CD39 was prepared in soluble form by deletion of two transmembrane domains and inclusion of a new leader sequence, and expressed in CHO cells[11]. This soluble CD39 (CD39) also blocked ADP-induced platelet aggregation in vitro[11]. The present studies were designed to elucidate the role of CD39 in the microvascular thrombosis of stroke, driven by the hypothesis that augmenting endogenous CD39 should inhibit ADP-mediated autoamplification of platelet recruitment in distal microvessels and thereby reduce accretion of thrombus stroke. The studies presented herein provide an improved method to use CD39 to inhibit microvascular thrombosis confer cerebroprotection in stroke without intracerebral hemorrhage.

Abbreviations: rtPA, recombinant tissue-type plasminogen activator; CBF, cerebral blood flow; ADP, adenosine diphosphate; $TXA_2$, thromboxane $A_2$; ICH, intracerebral hemorrhage.

Mice: Mice lacking CD39 were generated by homologous recombination in ES cells. Briefly, a gene targeting vector was created in which exons 3–5, containing Apyrase Conserved Regions 1–3 (ACR 1–3) were replaced with a PGK-neo cassette. The resulting targeting vector was introduced into 129 derived ES cells. ES clones carrying a CD39 allele disrupted by homologous recombination were identified by genomic Southern blot analyses and injected into blasdtocysts. The resulting chimeras were bred to C57BL/6 to generate mice heterozygous for the CD39 mutation (CD39+/−), which were subsequently intercrossed to generate mice deficient in CD39 (CD39−/− mice were born at the expected Mendelian frequency mice used throughout these experiments represent were on a background of 50% 129J; other mice used for experiments as indicated were CD39+/+ C57BL/6 mice or control C57BL/6/129J CD39+/+ mice (designated F1 controls: for clarity). Animals were 7–9 weeks of age and weighed between 22 and 26 g.

Materials: Specific materials were acquired form the following sources. ADP, heparin (Sigma, St. Louis, Mo.) collagen (Hormon Chemie, Munchen, Germany); sodium arachidonate (Nu-Check Prep, Elysian, Minn.).

Transient Middle Cerebral Artery Occlusion: Mice were anesthetized (0.3 ml if 10 mg/mL ketamine and 0.5 mg/mL xylazine, IP) and positioned supine on a rectal temperature controlled operating surface (yellow Springs Instruments, Inc). Animal core temperature was maintained at 37±2° C. during surgery and for 90 minutes after surgery. A midline neck incision was created to expose the right carotid sheath under the operating microscope (×6 to ×40 zoom, Leica). The common carotid artery was isolated with 4-o silk, and the occipital, pterygopalatine, and external carotid Artemis were each isolated and divided. MCAO was accomplished by advancing a 13-mm, heat-blunt tipped 6-0 nylon suture via an arteriotomy made in the external carotid stump. After placement of the occluding suture, the external carotid artery stump was cauterized to prevent bleeding through the arteriotomy, and arterial flow was established. The duration of carotid occlusion never exceeded 3 minutes. After 45 minutes, the occluding suture an cautery was once again employed to prevent bleeding through the arteriotomy. The wound was closed with surgical staples. These procedures have previously described in detail[25].

Measurement of Cerebral Cortical Blood Flow: Transcranial measurements of cerebral blood flow were made using laser Doppler (Permed, Inc. Piscataway, N.J.) as previously described[25]. Using a 0.7 mm straight laser Doppler probe (model PF 303, Perimed) and previously published landmarks (2 mm posterior to the bregma, 6 mm to each side of the midline)[25], relative cerebral blood flow measurement were made as follows; after anesthesia, immediately after occlusion, pre-reperfusion, immediate post-reperfusion, and at sacrifice. Data are expressed as the ratio of the Doppler signal intensity of the ischemic compared with the nonischemic hemisphere. The surgical procedure was considered to be technically adequate if a ≧70% reduction in cerebral blood flow was observed immediately after placement of the intraluminal occluding suture.

Neurological Exam: Twenty-four hours after surgery, mice were examined for neurological deficit using a modified four-tiered grading system published by Hata[26]. A score of 1 was given if the animal demonstrated spontaneous movements and extended both forelimbs when rolling supine (primitive Moro reflex); a score of two was given if the animal spontaneously circled clockwise when viewed from above; a score of three was given if the animal exhibited marginal activity and leaned to one side or had incomplete extension of the contralateral forelimb when rolled supine. A score of four was given if the animal exhibited no spontaneous movements.

Calculation of Infarct Volume: After neurological examination, mice were anesthetized, and final cerebral blood flow measurements obtained. Mice were sacrificed and brains were removed and placed in a mouse brain matrix (Activational Systems Inc.) For 1 mm sectioning. Section were immersed in 2% TTC (Sigma) in 0.9% saline, incubated for 12 minutes at 37° C. Infarcted brain was stained as an area of unstained tissue. Infarct volumes were calculated from digital images of 1 mm sections and expressed as the percentage of infarct in the ipsilateral hemisphere. This method of calculating infarct volumes has been used previously and has been correlate.

Preparation of CD39: Recombinant CD39 was prepared as described[11]. In brief, the CD39 cDNA insert, containing the CD39 sequence and IL-2 leader, was stably transfected into CHO cells, affinity purified from conditioned medium, followed by removal of N-linked sugars. Biochemical purity was assured as described[11]. Doses used are indicated in the test.

Measurement of Bleeding Time: Bleeding times were measured in mice which were not subjected to experimental manipulation other than by receiving either vehicle (saline) or CD39 prepared in physiological saline and administered intravenously 5 minutes prior to the experiment. Following anesthesia, a standardized incision was made on the central dorsal tail vein, and the tail was then immersed in physiological saline at 37.5° C. Time was recorded from the moment blood was observed to emerge from the wound until cessation of blood flow[29].

Measurements of cerebral thrombosis: $^{111}$Indium-platelet accumulation: Platelet accumulation was determined using $^{111}$Indium labeled platelets, collected and prepared as previously described [27,30]. In brief, pooled blood was collected from control mice in 3.8% sodium citrate for anticoagulation (10 mL total). Platelets were isolated by differential centrifugation, first at 300×g for 5 minutes to obtain platelet rich plasma, which was then washed three times at 2000×g for 15 minutes in 10 ml of acid/citrate/dextrose anticoagulant (ACD-A, containing 38 mmol/L citric acid, 75 mmol/L sodium citrate, and 135 mmol/L glucose). The pellet was suspended in 5 mL of ACD-A and centrifuged at 100×g for 5 minutes to remove contaminating red blood cells, and the supernatant was collected. $^{111}$In-oxyquinoline (70 μL of 1 mCi/mL, Amersham Mediphysics) was added, and the suspension was shaken gently for 30 minutes at room temperature. The radiolabeled platelets were washed three times in ACD-A and resuspended in PBS, and the platelet number was adjusted to 5×10$^6$ mL (1×10$^6$ counts were given to each animal). Immediately prior to insertion of the occluding suture, 0.2 mL of $^{111}$In-labeled platelet suspension was injected intravenously into the penile vein; at 24 hours of reperfusion, brain tissue was harvested and platelet accumulation was quantified as the ipsilateral/contralateral cpm ratio.

Detection of Intracerebral Fibrin: Mice were first subjected to focal cerebral ischemia and reperfusion as describe above. In order to detect fibrin by immunoblotting, mice were heparinized (1000U/ml, 0.2 mL given intravenously) about 1 minute prior to sacrifice) in order to minimize postmortem thrombosis. Following separation into right and left hemispheres and plasmin digestion to solubilize fibrin, immunoblotting for fibrin was performed as described previously[31] using a monoclonal anti-fibrin igG1 (Biodesign International, ME) that had been prepared with human fibrin-like beta peptide as immunogen. This antibody was shown to react with murine fibrin but not murine fibrinogen in preliminary experiments.

Measurement of intracerebral hemorrhage: ICH was quantified using a spectrophotometric assay for hemoglobin which has been recently developed and validated for use in a murine model of stroke [32]. In brief, mouse brains were homogenized, sonicated, centrifuged, and hemoglobin in the supernatants was converted (with Drabkin's regent) to cyanomethemoglobin, whose concentration was assessed by measuring O.D. at 550 nm against a standard curve generated with known amounts of hemoglobin.

Preparation of Murine Platelets: Mice (untreated, treated with 4 mg/kg CD39, or treated with 4 mg/kg aspirin) were anesthetized and heparinized (10 U/g), prior to blood collection via cardiac puncture performed with 22 gauge, 1 cc syringe. Immediately following collection, 80 µl 3.8% trisodium citrate was added to each mL of blood. Blood from 6–8 mice was pooled in a 15 mL tube centrifuge tube (Flacon, polypropylene). Platelet-rich plasma (PRP) was prepared with an initial whole blood centrifugation (900 g, 3 min, 20° C., no brake), and a second centrifugation of PRP (100 g, 2 min) to eliminate residual erythrocytes and leukocytes. The stock suspension of PRP was maintained at room temperature. PRP platelet counts were $400-700 \times 10^3$ platelets per µl.

Platelet aggregation studies: PRP (200 µl) was preincubated (3 min, 37° C.) with 100 µl Tris-buffered saline (TSG) buffer (15 mM Tris, 134 mM NaCl, 5 mM glucose, pH 7.4) in an aggregometer cuvette (Lumiaggregometer; Chrono-Log, Havertown, Pa.). After the 3 min, 37° C. preincubation $\approx 5.0 \text{ C } 10^5$ platelets, platelet agonist (ADP, collagen, sodium arachidonate) were added at the concentration indicated. Total volumes were adjusted to 300 µl with TSG buffer, and the aggregation response recorded for 2–4 min. Agonists were prepared as 100× solution: ADP was in TSG buffer, collagen in acidified isotonic glucose (German Chemie, Munchen, Germany), and sodium arachidonate in 0.85% saline. All aggregation studies were completed within two hours of blood collection.

Pharmacokinetic analysis: C57/6J BL mice (6–8 weeks of age; maintained under specific pathogen free conditions; Jackson Laboratory, Bar Harbor, Me.) were intravenously injected with 200 µg recombinant CD39. At the indicated times after injection (1 h, 6 h, 12 h, and 24 h) mice were bled by cardiac puncture, PRP was prepared as described above, and % platelet inhibition was documented at the respective timepoints. Aggregometry performed on the PRP samples was performed in triplicate.

Quantitation of Platelet Aggregation: Area under the curve was estimated by multiplying the height of the curve with its width at half height. The former was measured form pre-simulation baseline to the middle of the highest point of the curve. However, when curves were less than ⅓ of maximal height, the lowest point of the shape change portion of the curve was considered baseline. Width at half height was extrapolated if the curve did not re-approach baseline, but was always considered 6 min (=cm) or less. These criteria underestimate large aggregation responses, and overestimate small ones. Thus we knowingly underestimated the effects of compounds with great inhibitory capacity. This approach was preferred over one that could have overemphasized inhibitory potential.

Murine platelet aggregation: C57/6J BL mice (6–8 weeks) were obtained from Jackson Laboratories, Bar Harbor, Me.). Untreated mice, and mice treated with 4 mg/kg CD39, with 5 mg/kg aspirin or phosphate buffered saline, were anesthetized and heparinized (10 U/g), prior to blood collection via cardiac puncture; 80 µL 3.8% trisodium citrate was added to each mL of blood. Samples from 6–8 mice were pooled and platelet-rich plasma (PRP) prepared by centrifugation (900 g, 3 min, 20° C., followed by 100 g, 2 min to eliminate residual erythrocytes and leukocytes). PRP contained $400-700 \times 10^3$ platelets per µL. PRP (200 µL) was preincubated (3 min, 37° C.) with 100 µL Tris-buffered saline (TSG) buffer (15 mM Tris, 134 mM NaCl, 5 mM glucose, pH 7.4)[11,23,24] in an aggregometer cuvette (Lumiaggregometer; Chrono-Log, Havertown, Pa.). Platelet agonists (ADP, collagen (Hormon Chemie, Munchen, Germany), or sodium arachidonate (Nu-Check Prep, Elysian, Minn.)) were added at the final concentrations indicated. Aggregation responses were recorded for 2–4 min, and expressed as area under the curve (height times width at ½ height). All experiments were completed within two hours of blood collection.

EXAMPLE 2

Murine Stroke Model

A previously validated murine model of stroke injury was employed[2,3,25]. Anesthetized mice were maintained at 37±2° C. during and 90 min following surgery. A midline neck incision was made and the right carotid artery exposed. Middle cerebral artery occlusion was accomplished by advancing a 13-mm heat-blunt tipped 6-0 nylon suture via an arteriotomy in the external carotid stump. The external carotid artery was cauterized to secure hemostasis, and arterial flow re-established. Carotid artery occlusion never exceeded 3 min. The occluding suture was removed after 45 min and cautery was again locally applied to prevent bleeding at the arteriotomy site. Surgical staples were used for wound closure. Procedures for Doppler measurement of cerebral cortical blood flow, neurological score[26], calculation of infarct volume, measurement of cerebral thrombosis using $^{111}$In-labeled platelets[2,27], detection of intracerebral fibrin[2], and measurement of intracerebral hemorrhage[2,28] have been described in earlier section of this application.

EXAMPLE 3

Figure 1B:
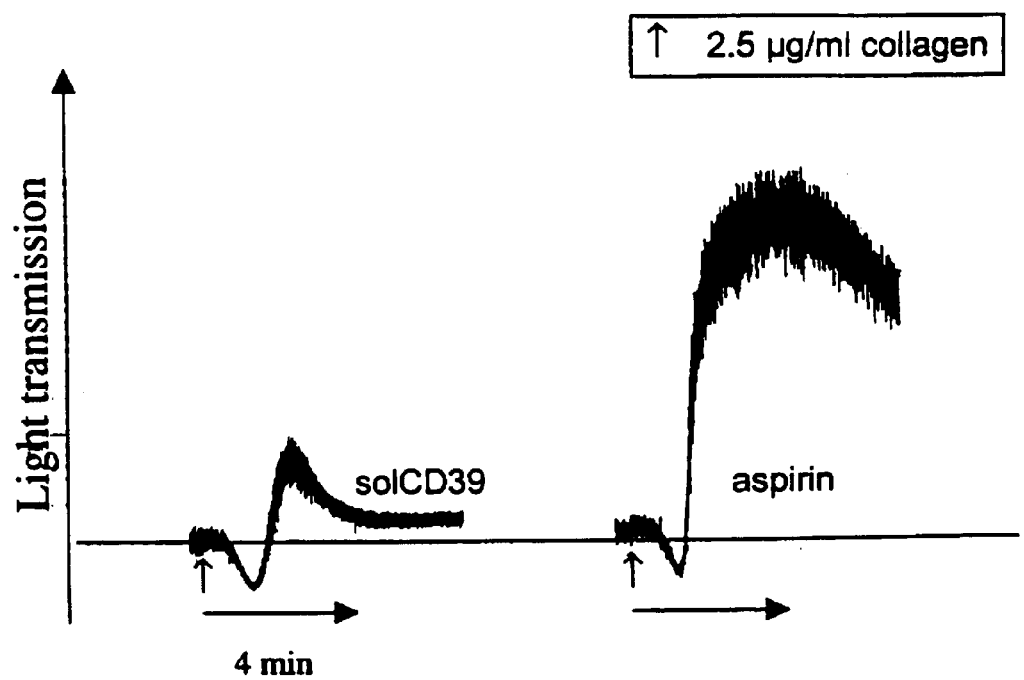
Figure 1C:
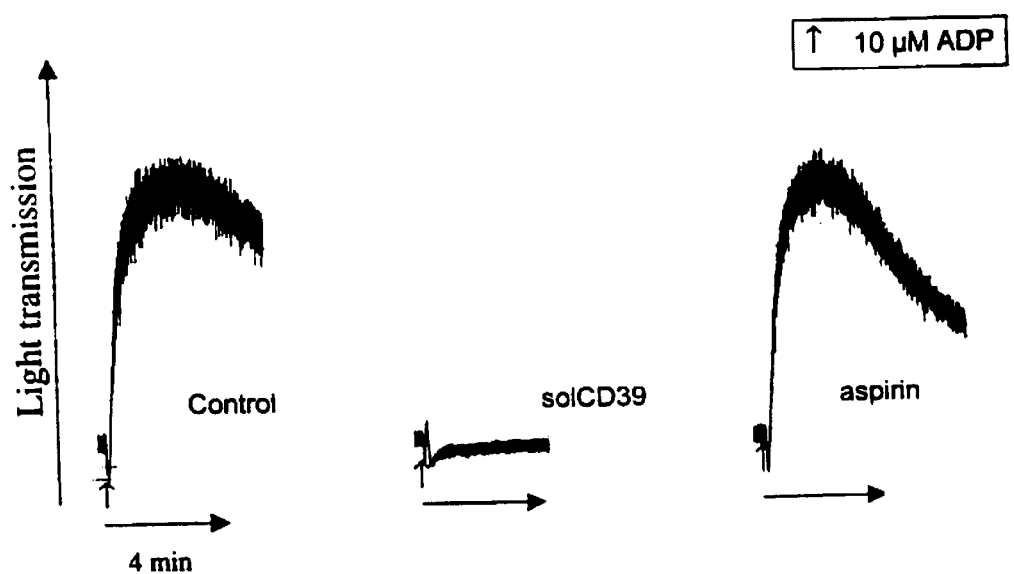
Figure 1D:
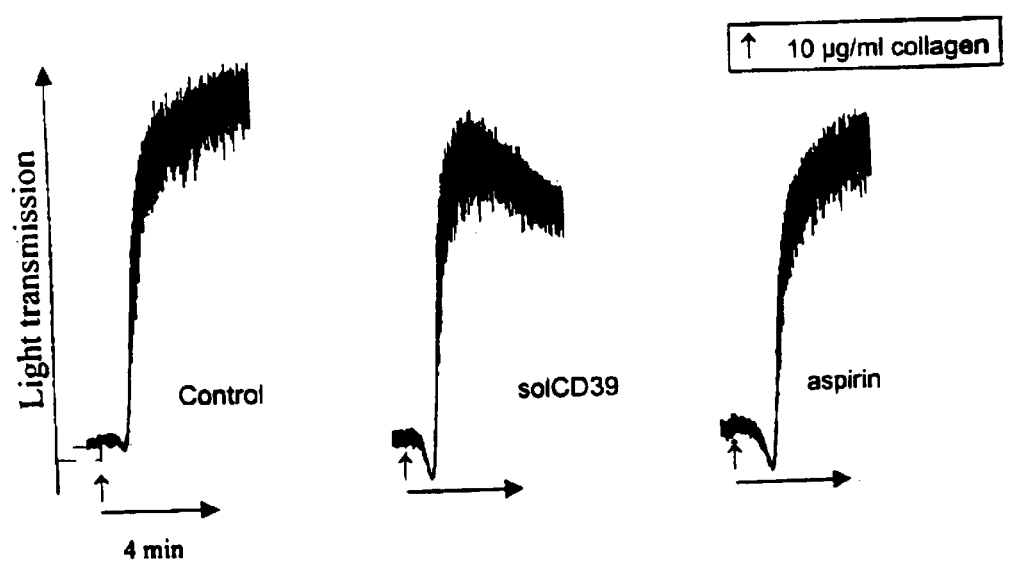
Figure 1E:
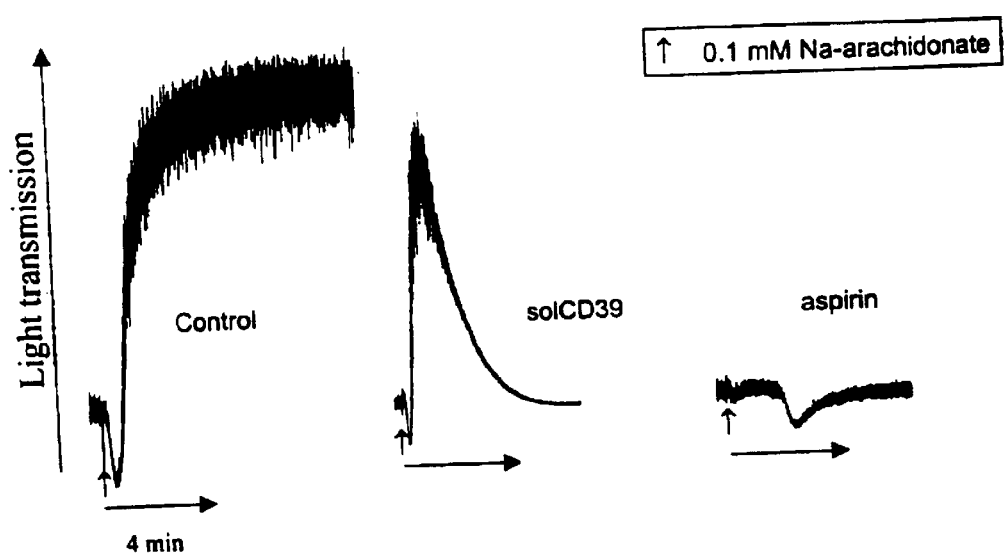
Figure 1F:
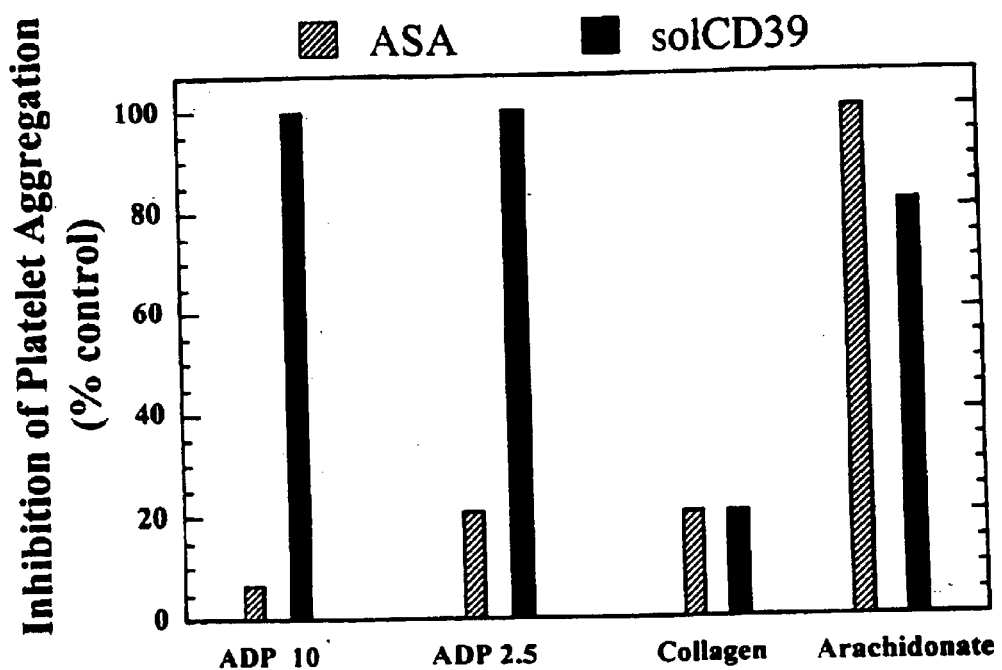

Recent studies have demonstrated that CD39 inhibits ADP-mediated platelet aggregation[11]. To ascertain the relative potency of CD39 and another agent thought to improve outcomes following transient cerebral attacks in human (aspirin[12]), aggregometry studies were performed using murine platelets treated with saline (control), CD39, or aspirin. Control and aspirin-treated platelets strongly aggregated in response to challenge with either ADP (FIGS. 1A & 1C) or collagen (FIGS. 1B & 1D). In sharp contrast, GD39 completely abrogated the platelet aggregation response to ADP addition, and attenuated the aggregation response to collagen (inhibition was greater with a lower of collagen). Dose-response data showed an increase in the response to sodium arachidonate, the precursor of thromboxane $A_2$ was somewhat different. As expected, aspirin abrogated the platelet response to arachidonate (FIG. 1E). CD39, on the other hand, did not inhibit the initial activation phase of platelet aggregation to arachidonate, but rapidly disaggregated platelets during the initial recruitment phase. The data are quantified to show percent inhibition of platelet aggregation in response to aspirin or CD39 treatment (FIG. 1F).

Figure 3A:
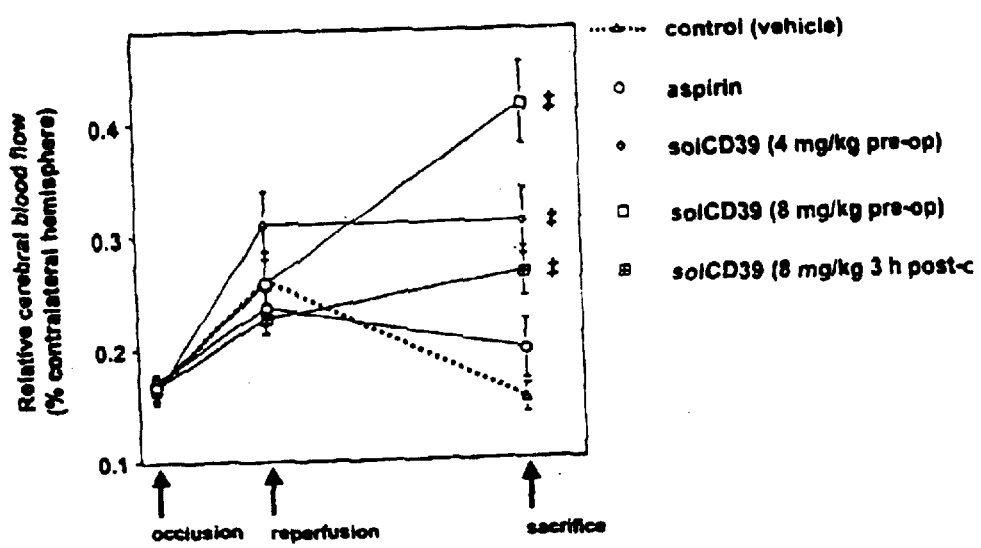
FIGS. 3A–3E: Effect of CD39 on stroke outcomes, and comparison with aspirin. (A) Cerebral blood flow; (B) cerebral infarction volume; (C) Neurological deficit stroke; (D) mortality; (E) intracerebral hemorrhage.
Figure 3B:
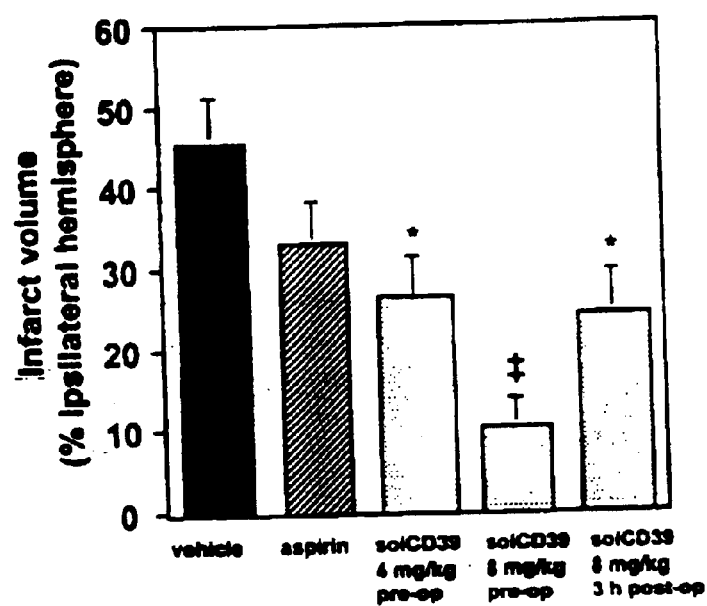
Figure 3C:
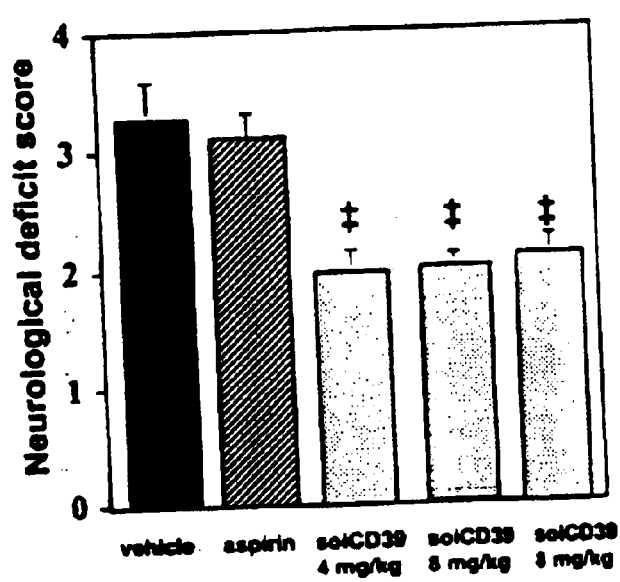
Figure 3D:
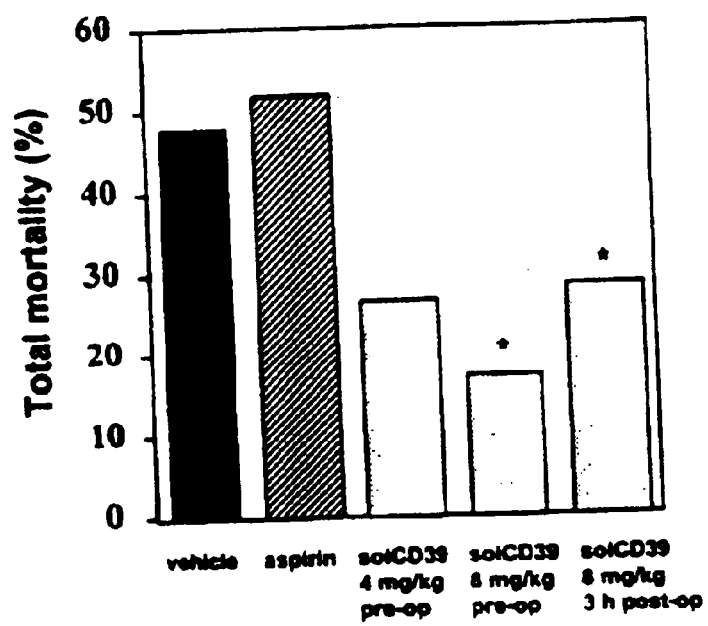

Reduction in sequelae of stroke by CD39: Experiments were performed to demonstrate the therapeutic utility of intravenously injected CD39 in stroke. CD39 inhibited platelet as well as fibrin accumulation in the ipsilateral cerebral hemisphere following induction of stroke (FIGS. 3A & 3B). As postulated, the ability of CD39 to reduce thrombosis was accompanied by improved postischemic cerebral perfusion (FIG. 3A). In contrast, aspirin, when administered at a clinically relevant dose that inhibited the ex vivo response of platelets to arachidonate, did not improve postischemic cerebral blood flow (FIG. 3A). Preoperatively administered CD39 conferred a dose-dependent diminution of cerebral infarct volume (FIG. 3B). In contrast, although aspirin showed a tendency to decrease cerebral infarct volume, the effect was not statistically significant. CD39 treatment (either prior to, or up to 3 hours following stroke) reduced both neurological deficit (FIG. 3C) and mortality (FIG. 3D).

EXAMPLE 4

Figure 3E:
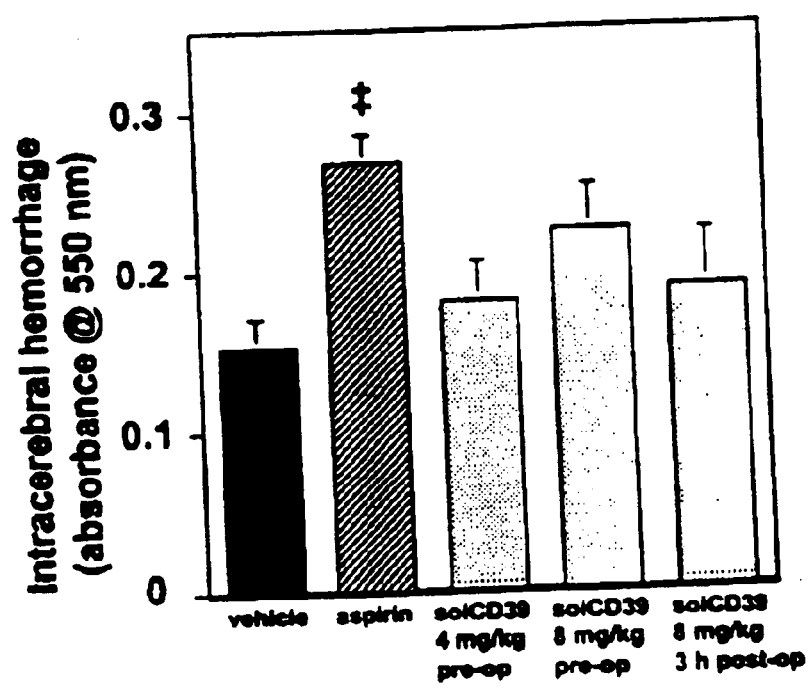
Figure 4:
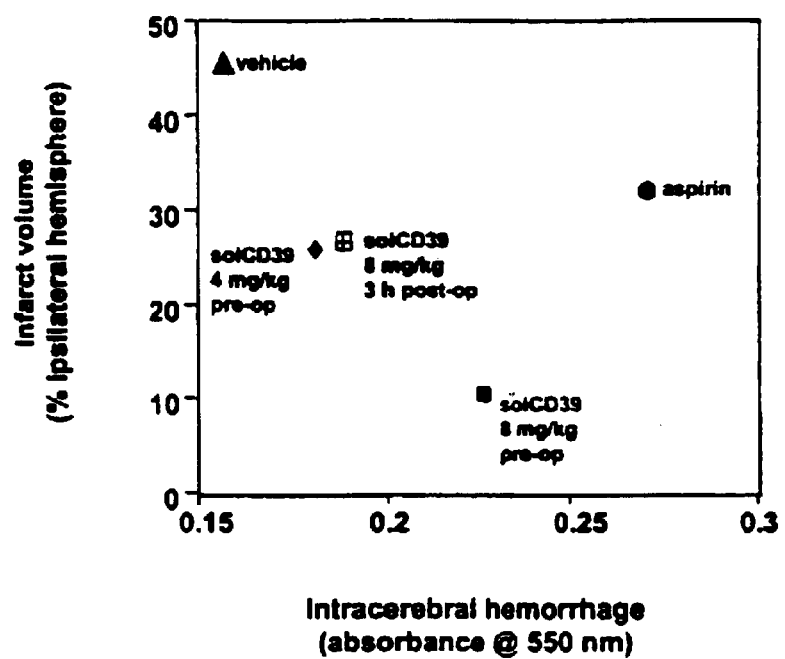
FIG. 4. Covariate plot of cerebral infarct volume vs intracerebral hemorrhage: Comparison of vehicle (saline) with aspirin (ASA, 5 mg/kg prior to stroke), CD39 (4 and 8 mg/kg prior to stroke), and CD39 (8 mg/kg, 3 hours following stroke induction).
Figure 5A:
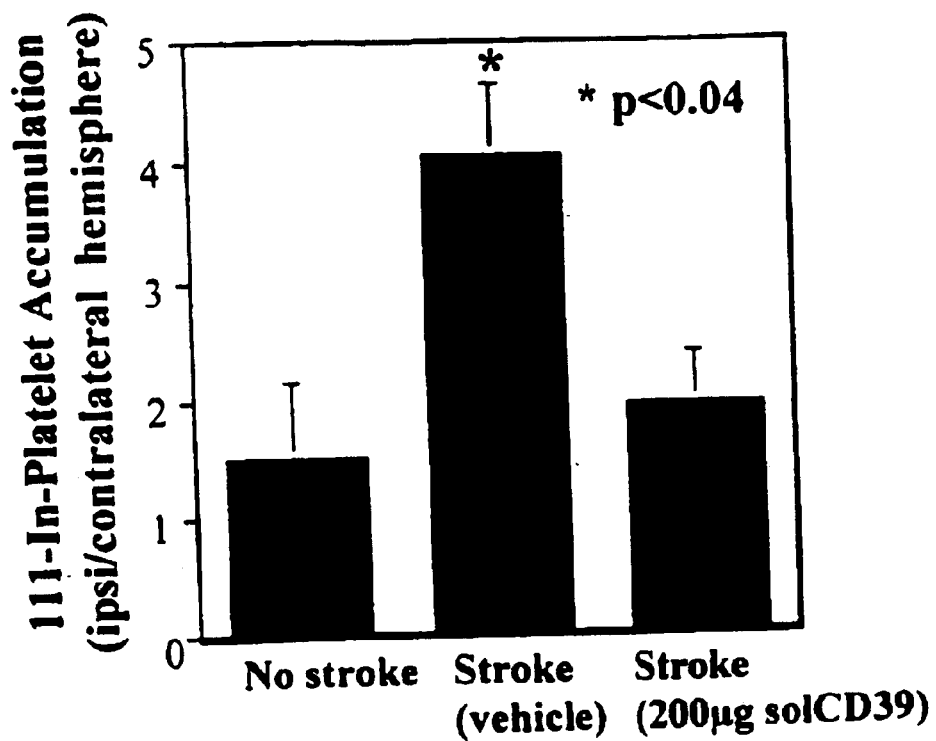
FIGS. 5A–5B: (A) Effect of CD39 on platelet deposition in stroke; (B) Effect of CD39 on fibrin accumulation in stroke; A positive fibrin control is shown in the leftmost lane. Ipsilat.=ipsilateral (i.e., ischemic) hemisphere. Contralat.=nonischemic left hemisphere.
Figure 5B:
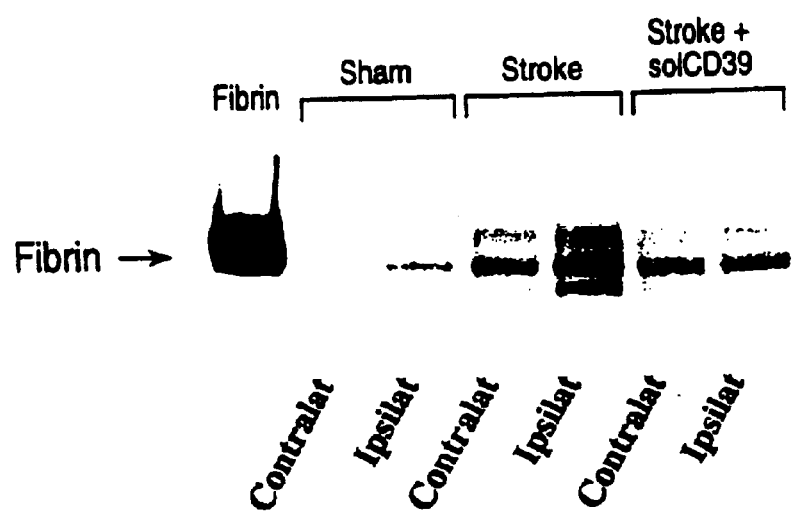

CD39 and aspirin were examined with regard to development of intracerebral hemorrhage following stroke (FIG. 3E). Whereas aspirin increased intracerebral hemorrhage significantly, there was no statistically significant increase in intracerebral hemorrhage at any dose of CD39 tested (FIG. 3E). At these doses CD39 inhibited both platelet and fibrin accumulation and promoted an increase in postischemic blood flow (FIGS. 3A, 5A & 5B). A covariate plot of cerebral infarct volume vs. intracerebral hemorrhage for each treatment indicates that aspirin is less capable of reducing infarct volume and preventing intracerebral hemorrhage than are several regimens of CD39 treatment (FIG. 4).

EXAMPLE 5

Figure 2:
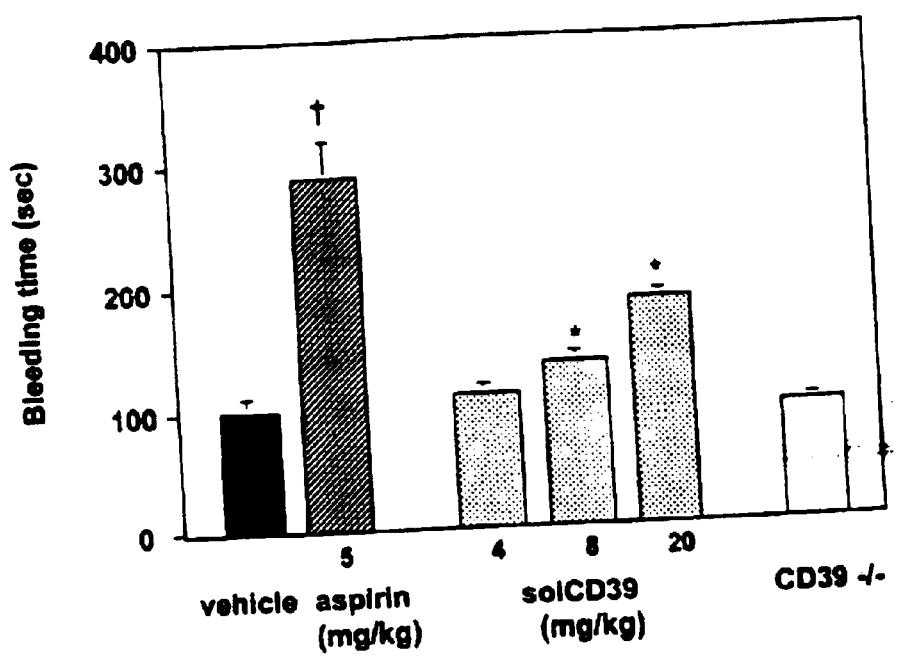
FIG. 2: Bleeding times in control, aspirin-treated, CD39-treated, or CD39 null mice.
Figure 6A:
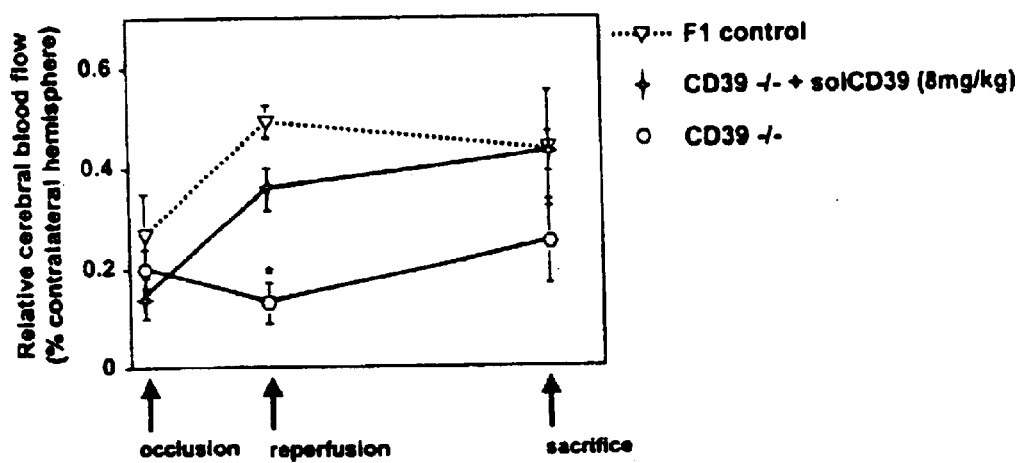
FIGS. 6A–6E. Comparison of stroke outcomes: control (C57BL/6J×129/J F1) mice (n=6), CD39−/− mice (n=5), and CD39−/− mice "reconstituted" with CD39 (n=6). Cerebral blood flow (A) cerebral infarct volume (B) neurological score (C) mortality, and (D) intracerebral hemorrhage (E) (*p<0.05, ‡p<0.01, †p<0.001).
Figure 6B:
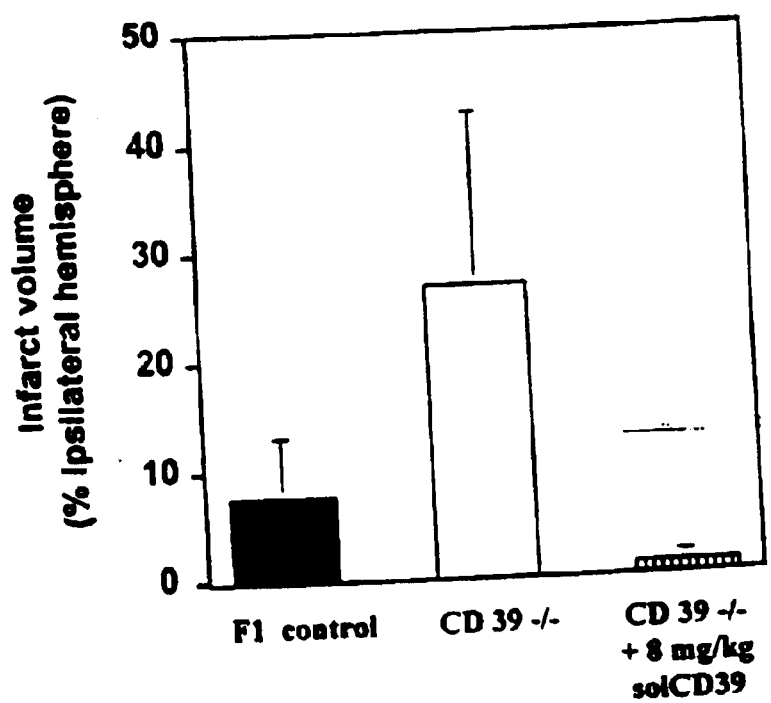
Figure 6C:
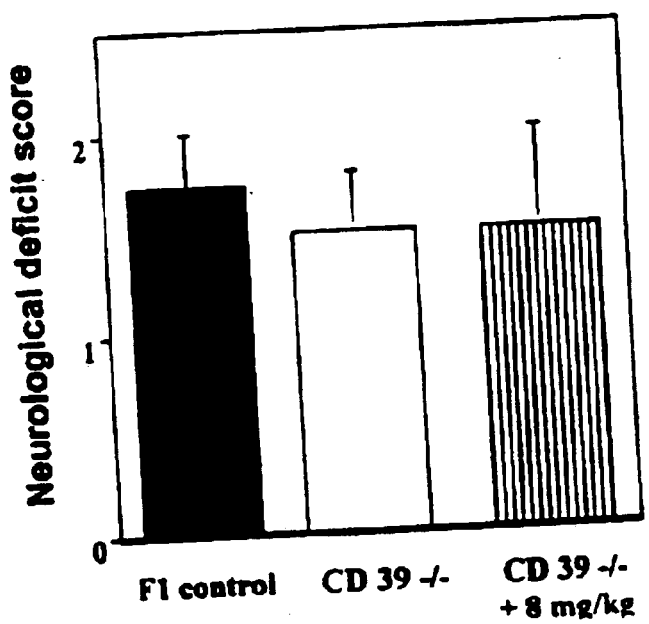
Figure 6D:
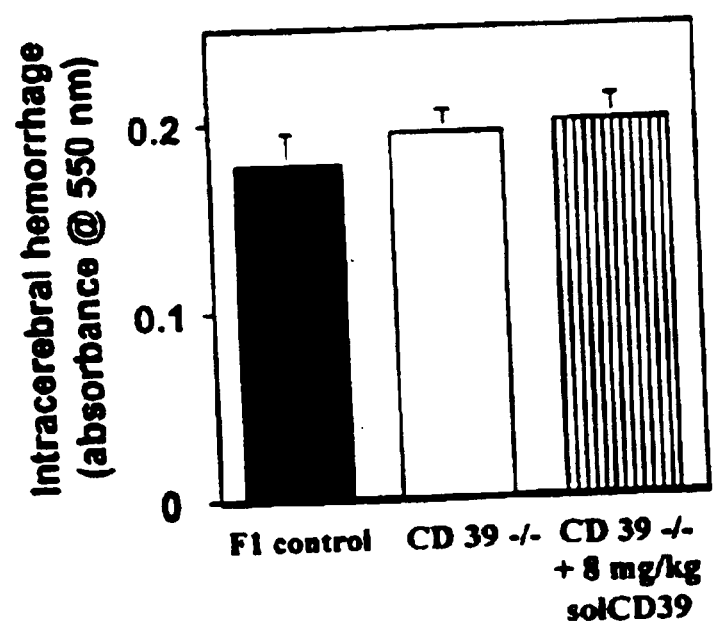
Figure 6E:
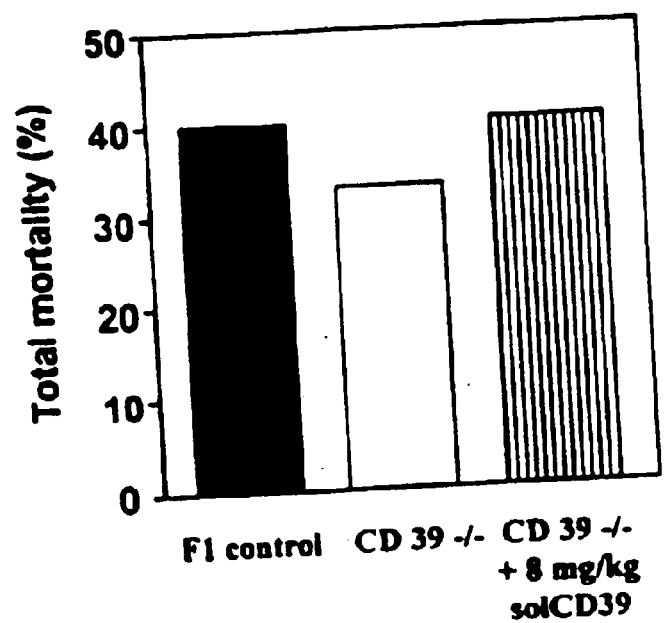

To further characterize the role of endogenous CD39 in regulation of hemostasis, CD39 null mice were generated by a gene targeting vector in which exons 3–5, containing Apyrase Conserved Regions 1–3 (ACR 1–3), were replaced with a PGKneo cassette. Homozygous null CD39 mice did not display an obvious phenotype in the unperturbed state, including normal bleeding times (FIG. 2). These bleeding times can be contrasted with unperturbed state, including normal bleeding times (FIG. 2). These bleeding times can be contrasted with the marked increase in bleeding time induced by aspirin treatment, and the dose-dependent increase in bleeding time evoked by CD39. Hematologic profiles, including platelet counts, hemoglobin levels, white blood cell counts and differentials (Table 1), and PT/PTT (not shown) were normal in these mice. To test the hypothesis that a latent prothrombotic phenotype could be induced in a clinically relevant platelet-dependent model (Stroke[2]), mice were subjected to focal cerebral ischemia. CD39 null mice exhibited diminished blood flow following reperfusion compared with their genetically matched controls (FIG. 6A). When CD39 (200 $\mu$g/mL was given to the CD39 null mice, these "reconstituted mice" exhibited postischemic flows which were similar to untreated control mice. When these null mice were sacrifices at 24 hours, there were increased cerebral infarction volumes compared with genotype-matched control mice. CD39 null mice reconstituted with CD39 were protected in stroke, as shown by their markedly diminished infarct volumes at 24 hours (FIG. 6B). Other parameters which were measured but which did not differ between groups included neurological deficit scores, overall mortality, and intracerebral hemorrhage, measured in a spectrophotometric hemoglobin assay which we have recently validated for use in stroke[32] (FIGS. 6C, 6D, & 6E).

EXAMPLE 6

Reconstitution of CD39−/− mice with CD39: To further characterize the contributions of endogenous CD39 to hemostasis and thrombosis, CD39−/− mice were generated by a gene targeting vector in which exons 4–6, encoding apyrase conserved regions 2–4[13-16], were replaced with a PGKneo cassette. Homozygous CD39−/− mice did not display an obvious phenotype in the unperturbed state. Hematological profiles were normal, including erythrocyte parameters, platelet counts, leukocyte counts and differentials, and coagulation screening tests. Bleeding times of CD39−/− mice were normal, in contrast to the markedly increased bleeding time following aspirin treatment, and a dose-dependent increase in bleeding time induced by CD39 (FIG. 2).

EXAMPLE 7

The next group of experiments were performed to demonstrate the utility of CD39 as a therapeutic agent in stroke. First, the antithrombotic action of CD39 was established by its ability to inhibit platelet accumulation in stroke (FIG. 5A) as well as to inhibit fibrin accumulation in the ipsilateral cerebral hemisphere (established by fibrin immunoblot (FIG. 5B). As expected, the ability of CD39 to diminish thrombosis in stroke was accompanied by improved postischemic cerebral perfusion (FIG. 3A). In contrast, aspirin, even when used at a clinically relevant dose which inhibited the response of platelets to arachidonate ex vivo, did not improve postischemic cerebral blood flow (FIG. 3A). In terms of cerebral infarction volume, CD39 administered preoperatively conferred a dose-dependent diminution of cerebral infarct volumes, in contrast to aspirin, which only tended to decrease cerebral infarct volumes (this reduction was not statistically significant) (FIG. 3B). Similarly, CD39 reduced both neurological deficit (FIG. 3C) and mortality (FIG. 3D). Of especial importance were data in which the effects of aspirin and CD39 were examined in terms of intracerebral hemorrhage. Although aspirin did increase intracerebral hemorrhage significantly, there was not statistically significant increase postischemic blood flow. The relationship between the ability of either aspirin, CD39, or vehicle to diminish cerebral infarction volume and their propensity to increase intracerebral hemorrhage are shown in FIG. 3.

EXAMPLE 8

Other forms of ischemia were also studied. Because of the integral role of platelets in other forms of coagulation, thrombosis, vascular remodeling (and disorders such as pulmonary embolism, lung ischemia, limb or gut ischemia, myocardial ischemia, post surgical vasculopathy, postangioplasty stenosis, shunt/fistula remodeling or thrombosis), I have tested the effect of CD39 in another ischemic disorder involving a different vascular bed than that in the brain. For these additional studies, I have used a mouse model of lung ischemia and reperfusion to show that CD39 confers significant postischemic protection to the lung tissues and blood vessels.

In these studies, murine ischemic reperfusion model was used. In the mouse model of lung ischemia, mice were initially anesthetized intraperitoneal with 0.1 mg/mouse weight (g) of ketamine and 0.01 mg/mouse weight (g) of xylazine, following by intraperitoneal continuous infusion of one third of the initial dose per hour using a syringe pump (model 100 series, KD Scientific Inc. Mass.). After ensuring appropriate depth of anesthesia, mice were intubated via tracheostomy and placed on a Harvard ventilator (tidal volume=0.75 mL, respiratory rate=120/min) with room air, followed by bilateral thoracotomy. The left hilum was cross-clamped for a period of 1 hour after which the cross-clamp was released. Reperfusion proceeded for 2 hours.

For all experiments, the surgical operator was blinded by a colleague in the laboratory to the specific substance being injected (vehicle or CD39, 8 mg/kg). Experimental procedures were as follows. After one-hour ischemia followed by 2-hour reperfusion, the contralateral (right hilum was permanently ligated, so that the animal's survival and gas exchange depended solely upon the reperfused lung, and observation continued for 1 hour. As the mouse continued to be ventilated, death of the mouse was defined as a combination of (1) cessation of regular cardiac activity; (2) the apparent collapse of the left atrium; and (3) brief clonic activity indicating cessation of cerebral blood flow.

In four experiments with CD39, mouse survival was 100% following functional removal of the contralateral (nonischemic) lung from the circulation. In contrast, control (vehicle-treated) (n=7) demonstrated no survival under identical conditions. These data indicate that CD39 has a marked protective effect (reduces tissue injury and protects function) of the postischemic lung.

Discussion

Platelet and fibrin deposition downstream of an occlusive lesion contribute significantly to the postischemic hypoperfusion and tissue injury complicating stroke. It has been demonstrated for the first time in vivo protection conferred by CD39 in this platelet-dependent thrombotic disorder. CD39 improves cerebral blood flow and reduces cerebral infarct volume when given preoperatively. In addition, CD39 confers significant cerebroprotection when administered three hours after onset of stroke. Rendering cerebroprotection at this delayed time point is significant because these effects occurred without an increase in mortality or intracerebral hemorrhage. The CD39-/- mice had a defect in thromboregulation in that they exhibited larger infarct volume than their genotype-matched controls. The CD39-/- mice were "reconstituted" by administration of CD39, thus fulfilling Koch's postulates[17].

CD39-/- mice did not have an obvious phenotype, with completely normal baseline hematological and coagulation profiles, including platelet counts. This contrasts with mice null for the protein P-selectin, where leukocytosis is apparent in unperturbed mice[18]. Moreover, spontaneous thrombotic events have not been observed, as reported in PAI-1 overexpressing mice[19]. Rather, CD39-/- mice appear to exhibit a latent prothrombotic phenotype, elicited by inducing a platelet-dependent thrombotic disorder (stroke). It is postulated that under basal conditions, vascular homeostasis may be maintained by the endothelial thromboregulators prostacyclin and nitric oxide[8]. However, a severe breach in vascular integrity leads to platelet accumulation and consequent fibrin deposition in the absence of CD39, as in the CD39-/- mice. Reconstitution of the animal with CD39 appears to ameliorate this defect (FIGS. 6A, 6B).

Although aspirin may be of benefit in primary prevention of stroke, it does not appear to be efficacious in evolving stroke[12]. Moreover, some patients obtain little benefit from aspirin ("nonresponders"), even though it is efficacious in others[10,20]. GPIIb/IIIa antagonists are potent inhibitors of platelet aggregation, since they block a final step in platelet accumulation, i.e. fibrinogen bridging of surface glycoprotein GP IIb/IIIa receptors, thus abrogating platelet-platelet adherence. Although useful in prevention of intravascular thrombosis following percutaneous coronary intervention, these agents have not been widely studied specifically in the setting of acute stroke. One highly specific GP IIb/IIIa antagonist, GPI-562, had potent antithrombotic effects in experimental stroke, and did reduce cerebral infarction volume, but it was associated with intracerebral hemorrhage[2]. Other platelet inhibitors useful in management of acute ischemic syndromes, such as ticlopidine or clopidogrel[21], inhibit platelet aggregation mediated by the low affinity P2Y1 ADP receptor on the platelet surface[22]. The data herein show that endogenous CD39 is protective in stroke, and that administration of pharmacological doses of CD39 is effective in inhibiting thrombosis and tissue injury in stroke. Since CD39 inhibits all ADP-mediated platelet aggregation via metabolic deletion of ADP from the activated platelet releasate, it may be more potent than the ADP-receptor blockers currently in use.

The basis for the apparent superiority of CD39 to aspirin may be that it induces more potent inhibition of ADP-induced platelet aggregation. This latter mechanism is more efficient in platelet-induced platelet recruitment than the arachidonate/thromboxane pathway. Moreover, while platelet reactivity to low-dose collagen is inhibited by CD39, platelets do respond to higher doses of collagen. In contrast, aspirin had little effect on platelet reactivity at any collagen dose. The hemogtatic effects of agonist-induced pathways are likely to overlap with considerable redundancy in vivo. However, the experimental data indicate that aspirin resulted in more bleeding in response to vein injury, or stroke, than did CD39. Perhaps the initial layer of platelets that adheres to an injured vessel wall is essential for hemostasis, but in stroke, ADP-mediated recruitment of platelets into an evolving thrombus results in intravascular occlusion. CD39 disaggregates platelets that have already responded to an agonist, but it does not have a deleterious effect on primary hemostasis.

It has been previously demonstrated that microvascular thrombosis is a continuing phenomenon after the onset of stroke[2]. Therefore, this ongoing process can be modulated by therapeusis with CD39, even three hours after stroke induction. The data presented herein are especially pertinent in the setting of clinical observations of increased intracerebral hemorrhage when thrombolytic agents are administered beyond three hours following stroke onset[6]. Thus, the results may constitute a possible new approach to antithrombotic therapy, based upon metabolism of a major agonist for vascular occlusion platelet-released ADP.

It was hypothesized that a latent prothrombotic phenotype could be identified in a clinically relevant platelet-dependent stroke model[2]. Indeed, CD39-/- mice, subjected to focal cerebral ischemia, did exhibit diminished blood flow following reperfusion as compared to genetically matched controls (FIG. 6A). When CD39 (8 mg/kg) was administered to the CD39-/- mice, these mice were "reconstituted" as shown by a postischemic blood flow similar to untreated controls. Furthermore, CD39-/- mice demonstrated increased cerebral infarction volume as compared to genotype-matched controls following induced stroke (FIG. 6B). CD39-/- mice "reconstituted" with CD39 had markedly diminished infarct volume, indicating a protective effect of CD39. Other parameters (neurological deficit scores, overall mortality, and intracerebral hemorrhage) did not differ between groups (FIGS. 6C, 6D, & 6E), Moreover, CD39 should inhibit only platelet/platelet recruitment mediated ADP, and attenuate recruitment by other agonists such as collagen or arachidonate. As CD39 does not interfere with the primary GPIb-mediated platelet adhesive event at the site of vessel damage, CD39 should not prevent a subsequent layer of platelets form forming at sites of vascular damage and therefore not interfere with hemostatic regulatory mechanisms required for prevention of intracerebral hemorrhage. I also hypothesized that alternative methods of inhibiting platelet-mediated amplification of intravascular thrombosis should provide a strategy in which primary hemostasis at sites of vascular injury may be maintained, in the setting of inhibition of platelet-mediated autoamplification (recruitment).

The experimental data indicate that platelet and fibrin deposition in the ipsilateral cerebral hemisphere contribute significantly to the postischemic hypoperfusion and tissue injury which occur in stroke. These studies identify for the first time an in vivo protective role conferred by CD39 in a platelet-dependent thrombotic disorder (stroke). CD39, which we show to be a potent inhibitor of ADP-induced platelet aggregation, also has an extended in vivo half life (elimination half-time in mice is 2 days[11]). Not only does it improve cerebral blood flow and reduce cerebral infarction volumes when given preoperatively, but it also confers significant cerebroprotection when given 3 hours after the onset of stroke The effect of this agent in conferring cerebroprotection at this delayed time point is both novel and important because the cerebroprotective effects occurred without increasing intracerebral hemorrhage or mortality. The CD39 null mice, which exhibit larger infarct volumes than their genotype controls, were rescued by the administration of CD39, fulfilling Koch's postulates[32] for demonstration that endogenous CD39 is a major thromboregulator.

CD39 is a 95 kD integral endothelial cell membrane glycoprotein, comprised of two membrane spanning domains, a centrally located hydrophobic domain, and four putative ADPase (apyrase) domains which are highly conserved[11]. CD39 is constitutively expressed on vascular endothelial cells, and appears to exert an important antithrombotic activity on the endothelial cell surface. This enzyme degrades nucleotide tri- and diphosphates (but not monophosphates), and hence its expression at the endothelial surface significantly blunts the ADP-mediated recruitment phase of platelet reactivity[11]. In vitro studies have shown that COS cells transfected with the cDNA encoding human CD39 acquired the ability to inhibit ADP-induced platelet aggregation[9]. As the initial step toward developing a potentially useful antiplatelet therapeutic agent, a recombinant soluble from of CD39 was prepared by transfecting CHO cells with a cDNA construct containing the four apyrase domains but lacking the two transmembrane regions of native CD39 and introducing a leader sequence. The resulting peptide, isolated from conditioned medium was affinity purified and shown to retain potent apyrase activity, and to have an elimination half-time in mice of 2 days[11]. It was this peptide, CD39, which was used in the experiments described here. These studies confirm the ex vivo platelet inhibitory activity of CD39. However, the current results extend the initial observations in two ways: 1) I demonstrated platelet inhibitory activity after administration in vivo; and 2) I documented the effect of CD39 on primary hemostasis (dose-dependent increase in bleeding time, and reduction of thrombosis in stroke).

In addition to demonstrating the effects of pharmalogical doses of CD39, to our knowledge, the current studies are the first to characterize the properties of CD39 null mice. These mice do not have an obvious phenotype. Unlike mice null for other unrelated alleles, such as P-selectin, in which leukocytosis is apparent in unperturbed mice[1], baseline hematologic and coagulation profiles in these mice are completely normal (including platelet counts). In addition, I have not observed spontaneous thrombotic events, such as those seen in PAI-1 overexpressing mice[33] which may exhibit spontaneous ischemic events resulting in lost digits or the tip of the tail. Rather, CD39 null mice to exhibit a latent prothrombotic phenotype. By inducing a platelet-dependent thrombotic disorder (stroke), I was able to elicit differences between appropriate genetic control mice and CD39 null mice.

There is an important point to be considered in the setting of the data presented herein. We and others have previously shown that in studies of mice, uniformity of background strain is critical for stroke research. Importantly, baseline cerebral infarct volumes were smaller in the CD39 mice on the 129/C57Bl background than in control mice which were pure C47Bl/6J. Because of limitations in time for backbreeding, the CD39 null mice which were used for the current experiments are on a mixed background (C57Bl/129J). Therefore, genotype-matched control mice were essential to establish the latent prothrombotic phenotype of these mice and their relative susceptibility to cerebral infarction. Data were also obtained or derived from experiments using pure C57Bl/6J mice. As one would expect from published literature, C57Bl/6J mice have larger absolute cerebral infarction volumes than "F1 control" mice comprised of a mixed C57Bl/6J/129J background; therefore, it is important to compare data only with genotype-matched controls. It has been shown that there are reproducible strain-related differences in susceptibility to stroke. Thus, 129J is a particularly resistant strain, and C57Bl is a particularly susceptible strain[25,34,35]. For this reason, genetically matched controls were performed.

Why should CD39 constitute a better therapeutic strategy in stroke than other anti-platelet agents, with greater or lesser efficacy different mechanisms of actions? Aspirin, which has clear benefits in terms of primary prevention of stroke, has not been shown to be efficacious for evolving stroke[12]. Furthermore, there are a group of patients who are aspirin nonresponders[36], who obtain little benefit from aspirin even where it is efficacious in others. GPIIb/IIIa antagonist which was tested in stroke, GPI-562, had potent antithrombotic action and could diminished cerebral infarction volumes[2]. However, the therapeutic window for this agent was narrow. Thus only modest increases in dosage were associated with unacceptably high rates of intracerebral hemorrhage. Although not specifically tested in current experiments, other antiplatelet agents may be useful in the treatment of evolving stroke. This includes agents such as ticlodipine or clopidogrel, both of which inhibit platelet aggregation mediated by the low-affinity type II ADP receptor on the platelet surface. Experiments with the CD39 null mice and recombinant CD39 show that endogenous CD39 is protective, and the administration of pharmacologic doses of CD39 are effective in terms of inhibiting thrombosis and tissue injury during stroke. It remains to be seen whether so139 is more potent than the other ADP-receptor blockers, but CD39 should inhibit all ADP-mediated platelet aggregation. Unlike ticlodipine or clopidogrel, CD39 metabolically deletes ADP from an activated platelet releasate.

Data obtained in the experiments give insights into reasons for the superiority of CD39 to aspirin. First, it is clearly a more potent antiplatelet agent with respect to ADP-induced platelet aggregation, which may be of more importance in platelet-induced platelet recruitment than the arachidonate/thromboxane axis. Secondly, CD39 did not inhibit reactivity of platelets to low-dose collagen, although at high dose collagen, there was minor inhibition of collagen-induced platelet reactivity. Aspirin had no effect on collagen-reactivity of platelet at any collagen dose. The hemostatic effects agonist-induced pathways are likely to overlap with considerable complexity in vivo; however, experimental data on bleeding time and intracerebral hemorrhage indicated that aspirin was more potent as an anticoagulant in response to specific stimuli (such as cutting a vein, or stroke) than was CD39. Perhaps the initial layer of platelets which is laid down is essential for hemostasis, but the augmented accumulation of platelets via recruitment results in the intravascular obstruction which is deleterious in stroke. In this regard, CD39 is capable of disaggregating platelets which have already aggregated in response to all agonists.

How might CD39 prove to be therapeutically useful? It has been shown that the therapeutic index of CD39 is high, i.e., even twice the effective dose does not increase the occurrence of intracerebral hemorrhage. Furthermore, when given even 3 hours following stroke, therapeutic efficacy is apparent. These data confirm previous research in which microvascular thrombosis was demonstrated to be an ongoing process after the onset of stroke. Inhibition of ongoing microvascular thrombosis is the therapeutic target of the current CD39 strategy. These results are especially important in light of current clinical observation, which show increased intracerebral hemorrhage and mortality if a thrombolytic agent is administered beyond three hours following the onset of stroke. Even in the best of circumstances, few patients arrive at an emergency room in sufficient time to qualify for thrombolytic therapy[6]. An extended time window for administration of a therapeutically useful agent may be an important first step towards improving the current limited treatment paradigms for evolving stroke. CD 39 may also have an inhibiting effect on white blood cell accumulation or lucolyte accumulation Table 1: Hematological profiles of CD39−/− and genotype-matched control mice. N=f for each group.

5. Wardlaw, J. M., et al. (1997) "Systematic review of evidence on thrombolytic therapy for acute ischemic stroke [see comments]" Lancet., 350: 607–614;
6. Chiu, D., et al. (1998) "Intravenous tissue plasminogen activator for acute ischemic stroke: feasibility, safety, and efficacy in the first year of clinical practice" Stroke, 29: 18–22;
7. Marcus, A. J. & Safeir, L. B. (1993) "Thromboregulation: multicellular modulation of platelet reactivity in hemostasis and thrombosis" FASEB J., 7: 516–522;
8. Marcus, A. J. (1999) "in Inflammation: Basic Principles and Clinical Correlates" (EDS Gallin, J. I. & Snyderman, R.) 77–95 (Lippincott, Williams & Wilkins, Philadelphia;
9. Marcus, A. J., et al. (1997) "The endothelial cell ecto-ADPase responsible for inhibition of platelet function is CD39" J. Clin. Invest., 99: 1351–1360;
10. Harbison, J. W. Am. J. Health Syst. Pharm 55, S17–S20 (1998).
11. Gayle, R. B., et al. (1998) "Inhibition of platelet function by recombinant soluble ecto-ADPase/CD39" J. Clin. Invest, 101: 1851–1859;
12. Dippel, D. (1998) "The results of CAPRIE, IST, and CAST" Thrombosis Res., 92: S13–S16;
13. Handa, M. & Guidotti, G. Biochem. Biophys. Res. Commun. 218, 916–923 (1996).
14. Wang, T. F. & Guidotti, G. J. Biol. Chem. 271, 9898–9901 (1996).
15. Maliszewski, C. R., et al. (1994) J. Immunol., 153: 3574–3583;
16. Schoenborn, M. A., et al. (1998) "Cytogen Cell Gen., 81(3–4): 287–280;
17. Koch, R. Verhandlungen des X. Internationalem Medizinischen Congresses Berlin 1: 35–47 (1891).(Abstract)
18. Mayadas, T. N., et al. (1993) "Leukocyte rolling and extravasation are severely compromised in P-selection deficient mice" Cell, 74(3): 541–554;
19. Erickson, L. A., et al. (1990) Nature, 346: 74–76;
20. Grotenmeyer, K. H. Thrombosis Res., 63: 587–593 (1991);

TABLE 1

Comparison of Blood Cell Components in Wildtype versus CD39-deficient Mice.

| Strain | Hgb (mg/dl) | WBC (cells/ $\mu l \times 10^3$) | Plts (cells/ $\mu l \times 10^3$) | Segs (cells/ 100 WBCs) | Bands (cells/ 100 WBCs) | Lymphs (cells/ 100 WBCs) | Monos (cells/ 100 WBCs) | Eos (cells/ 100 WBCs) |
|---|---|---|---|---|---|---|---|---|
| CD39 +/+ | 13.6 ± 1.25 | 5.4 ± 0.74 | 799 ± 98.0 | 42 ± 2.0 | 1 ± 0.20 | 52 ± 2.4 | 5.2 ± 0.66 | 0.8 ± 0.37 |
| CD39 −/− | 13.2 ± 0.57 | 3.5 ± 0.40 | 776 ± 52.2 | 32.6 ± 3.4 | 0.4 ± 0.24 | 61.8 ± 3.2 | 5 ± 0.45 | 0.2 ± 0.2 |
| p-value | 0.47 | 0.11 | 0.82 | 0.39 | 0.37 | 0.28 | 0.85 | 0.21 |

References

1. Bronner, L. L., et al. (1995) "Primary prevention of stroke" N. Engl. J. Med. 333(21): 1392–1400;
2. Choudhri, T. F., et al. (1998) "Reduced microvascular thrombosis and improved outcome in acute murine stroke by inhibiting GP IIb/IIIa receptor-mediated platelet aggregation" J. Clin. Invest., 102: 1301–1310;
3. Connolly, E. S. Jr., et al. (1996) "Cerebral protection in homozygous null ICAM-1 mice after middle cerebral artery occlusion. Role of neutrophil adhesion in the pathogenesis of stroke" J. Clin. Invest., 97: 209–216;
4. Connolly, E. S. Jr., et al. (1997) "Exacerbation of cerebral injury in mice which express the P-selectin gene: identification of P-selectin blockade as a new target for the treatment of stroke" Circ. Res., 81: 304–310;
21. CAPRIE Steering Committee, Lancet., 348: 1329–1339 (1996);
22. Hechler, B., et al. (1998) Br. J. Haematol., 103: 858–866;
23. Broekmann, M. J., et al. (1991) Blood, 78: 1033–1040;
24. Marcus, A. J., et al. (1991) J. Clin. Invest., 88: 1690–1696;
25. Connolly, E. S. Jr., et al. (1996) "Procedural and strain-related variables significantly affect outcome in a murine model of focal cerebral ischemia" Neurosurg., 38(3): 523–532;
26. Huang, Z., et al. (1994) "Effects of cerebral ischemia in mice deficient neuronal nitric oxide synthase" Science, 265: 1883–1885;
27. Naka, Y., et al. (1995) "Enhanced preservation of orthotopically transplanted rat lungs by nitroglycerin but not hydralazine. Requirement for graft vascular homeostasis beyond harvest vasodilation" Circ. Res., 76: 900–906;

28. Choudhri, T. F., et al. (1997) "Use of a spectrophotometric hemoglobin assay to objectively quantify intracerebral hemorrhage in mice" Stroke, 28: 2296–2302;
29. Bowie E. J. W., et al. (1974) "Progress in Hemostasis and Thrombosis" The Bleeding Time, in Spaet TH (ed) 2d Ed, New York, Grune &Statton, pp249–271;
30. Mizutani H, et al. (1990) "Analyses of thrombocytopenia in idiopathic thrombocytopenic purpura-prone mice by platelet experiments between (NZW X BXSB)F1 and normal mice" Blood, 75:1809–1912;
31. Lawson C. A., et al. (1997) "Monocytes and tissue factor promote thrombosis in a murine model of oxygen deprivation" J. Clin. Invest., 99: 1729–1738;
32. Kock R. (1890) "Ueber bakteriologische Forschung" In VerhX Int Med Congr Berlin, 1892:35–30;
33. 21.Eitzman D. T. (1996) "Bleomycin-induced pulmonary fibrosis in transgenic mice that either lack or overexpress the murine plasminogen activator inhibitor-gene" J. Clin. Invest., 97:232–237;
34. Maeda K, et al. (1998) "Differences in the cerebrovascular anatomy of c57black/6 and SV129 mice" Neuroreport, 9(7):1317–1319;
35. Majid A., et al. (1999) "Intrinsic, hemodynamic-independent differences in vulnerability to permanent focal cerebral ischemia in common mutant mouse strains" 24th American Heart Association International Conference on Stoke and Cerebral CXJO-XXPY;
36. Buchanan M. R., et al. (1995) "Individual variation in the effects of ASA on platelet function: Implication for the use of ASA clinically" Cardiovasc. Medicine, 11(3) : 221–227.

What is claimed is:

1. A method for treating or preventing stroke in a human subject susceptible to intracerebral hemorrhaging, comprising administering to the human subject an effective amount of a CD39 polypeptide comprising consecutive amino acids the sequence of which is set forth in SEQ ID NO:2 so as to inhibit adenosifle diphosphate-mediated platelet aggregation by increasing adenosine diphosphate catabolism without increasing incidence of intracerebral hemorrhage in the human subject.

2. The method of claim 1, whereir the administration of the CD39 polypeptide occurs at the onset of stroke in the subject.

3. The method of claim 1, wherein the administration of the CD39 polypeptide is prior to stroke onset in the subject.

4. The method of claim 1, wherein the administration of the CD39 polypeptide occurs after the onset of stroke in the subject.

5. The method of claim 1, wherein the CD39 polypeptide is administered in a dosage of 1–20 mg/kg of the subject's body weight.

6. The method of claim 1, wherein the CD39 polypeptide is administered in a dosage of 4—8 mg/kg of the subject's body weight.

* * * * *